US008119690B2

(12) United States Patent
Fortin

(10) Patent No.: US 8,119,690 B2
(45) Date of Patent: Feb. 21, 2012

(54) POLYUNSATURATED FATTY ACID MONOGLYCERIDES, DERIVATIVES, AND USES THEREOF

(75) Inventor: Samuel Fortin, Ste-Luce (CA)

(73) Assignee: Centre de Recherche sur les Biotechnologies Marines, Rimouski (CA)

( * ) Notice: Subject to any disclaimer, the term of this patent is extended or adjusted under 35 U.S.C. 154(b) by 163 days.

(21) Appl. No.: 12/534,439

(22) Filed: Aug. 3, 2009

(65) Prior Publication Data

US 2009/0292019 A1    Nov. 26, 2009

Related U.S. Application Data

(63) Continuation-in-part of application No. PCT/CA2008/000301, filed on Feb. 14, 2008.

(60) Provisional application No. 60/889,984, filed on Feb. 15, 2007.

(51) Int. Cl.
*A61K 31/22* (2006.01)
*A23D 9/00* (2006.01)

(52) U.S. Cl. ........................................ 514/549; 554/224

(58) Field of Classification Search .................. 514/549; 554/224
See application file for complete search history.

(56) References Cited

U.S. PATENT DOCUMENTS

| 7,138,431 B1 | 11/2006 | Chilton |
| 2002/0188024 A1 | 12/2002 | Chilton et al. |
| 2004/0214799 A1 | 10/2004 | Mukai et al. |
| 2009/0291102 A1 | 11/2009 | Fortin |
| 2010/0160261 A1 | 6/2010 | Fortin |
| 2010/0196496 A1 | 8/2010 | Fortin |

FOREIGN PATENT DOCUMENTS

| WO | 02064166 | 8/2002 |
| WO | 02089787 | 11/2002 |
| WO | 02096408 | 12/2002 |
| WO | 2004024136 | 3/2004 |
| WO | 2004064716 | 8/2004 |
| WO | 2006/117668 | 11/2006 |
| WO | 2008036353 | 3/2008 |

OTHER PUBLICATIONS

Watanabe et al. CAS: 139:350107, 2003.*
Schaaf et al. CAS: 133: 161886, 2000.*
Schaaf et al., "Polyunsaturated monoglycerides and a pregnadiene in defensive glands of the water beetle *Agabus affinis*". Department of Aimal Ecology II, University of Bayreuth, Bayreuth, Germany. Lipids (2000), 35(5), 543-550.
Vandevoorde et al. Influence of the degree of unsaturation of the acyl side chain upon the interaction of analogues of 1-arachidonoylglycerol with monoacyglycerol lipase abd fatty acid amide hydrolase. Department of Pharmacology and Clinical Neuroscience, Umea University, Umea, Swed. Biochemical and Biophysical Research Communications (2005), 337(1), 104-109. Publisher: Elsevier.
Akoh, Casimir C., Lipase-catalyzed synthesis of partial glyceride. Dep. Food Sci. Technol., Univ. Georgia, Athens, GA, USA. Biotechnoloy Letters (1993), 15(9), 949-954.
An English abstract of JP2000044588. Yagi et al. Novel monoacylglycosyl monoacylglycerols for surfactants. (Agency of Industrial Sciences and Technology, Japan) Jpn. Kokai Tokkyo Koho (2000), 7 pp. CODEN.
Rosu et al., "Enzymic synthesis of glycerides from DHA-enriched PUFA ethyl ester by glycerolysis under vacuum". Graduate school of Bio- and Agro-Sciences, Laboratiry of Molecular Biotechnology, Nagoya University, Nagoya Japan. Journal of Molecular Catalysis B. Enzymatic (1988), 4(4), 191-198.
Yamane et al. "Mutiple intensified performance of an enzyme-catalyzed reaction in organic medium". Laboratory of Molecular Biotechnology Graduates School of Bio- and Agro-Sciences, Nagoya University, Nagoya, Japan. Annals of the New York Academy of Sciences (1988), 864 (Enzyme Engineering XIV), 171-179.
Ando et al., "Reinvestigation of positional distribution of fatty acids in docosahexaenoic acid-rich fish oil triacyl-sn-glycerols". Deparment of Marine Bioresources Chemnistry, Faculty of Fisheries, Hokkaido Universit, Hakodate, Japan. Lipids (2000), 35(5), 579-582.
Kawashima et al., "Enzymatic synthesis of high-purity structured lipids with caprylic acid at 1,3-positions and polyunsaturated fatty acid at 2-positin". Sonoda Wowen's Junior College, Hyogo, Japan. Journal of the American Oil Chemists' Society (2001) 78(6), 611-616.
Watanabe et al. "n-3 Polyunsaturated fatty acid (PUFA) deficiency elevates and n-3 PUFA enrichment reduces brain 2-arachidonoyglycerol level in mice" Institute of Natural Medicine, Department of Clinical Application, Toyama Medical and Pharmaceutical University, Toyama, Japan. Prostaglandins Leukotrienes and Essential Fatty Acids (2003), 69(1), 51-59.
Watanabe et al., "Chemical signals involved in larval metamorphosis in Hydroides Ezoensis (Serpulidae; Polychaeta). Part II: isolation and identification of a new monoacyl Glycerol from adult tube clumps as a metamorphosis-including substance". Department of Applied Biological Chemistry, Faculty of Agricultur, Shizuoka University, Shizuoka, Japan. Journal of Marine Biotechnology (1998), 61(1), 11-15.
A partial English translation of Tanaka et al., Preparative separation of acylglycerol by cebtrifugal partition chromatography (CPC). Tsukuba Res. Lab., Nippon Oil and Fats Co., Ltd., Tsukuba, Japan. Yukagaku (1992), 41(1), 23-7.
Feng Li et al., "Biosynthesis of Docosahexaenoate-Containing Glycerolipid Molecular Species in the Retina" Journal of Molecular Neuroscience (2001), vol. 16, 206-214.
An English abstract of JP7149786 of Yazawa et al., "Glyceroglycolipid and Carcinogenic Promoter Inhibitor", published on Jun. 13, 1995.

(Continued)

*Primary Examiner* — Rei-tsang Shiao
(74) *Attorney, Agent, or Firm* — Bereskin & Parr/S.E.N.C.R.L., s.r.l.

(57) ABSTRACT

There are provided various polyunsaturated fatty acid monoglycerides and derivatives thereof. These compounds can be useful as cancer chemopreventive agents, cancer treating agent, inhibiting tumor growth or cell proliferation, reducing tumor growth or as radioenhencers for radiotherapy of cancer.

21 Claims, 6 Drawing Sheets

OTHER PUBLICATIONS

Zerouga et al., "Synthesis of a Novel Phosphatidylcholine Conjugated to Docosahexaenoic Acid and Methotrexate that Inhibits Cell Proliferation" Anti-Cancer Drugs (2002), 13, pp. 301-311.

An English Abstract of JP 02131418 of Okazaki et al., "Comparison of Enhanced and Routine Methods for Measuring Ambient Low-Level Sulfur Dioxide". (Sansei Pharmaceutical Co., Ltd., Japan.) Jpn. Kokai Tokkyo Koho (1980), 7 pp.

Monks, A., "Feasibility of a High-Flux Anticancer Drug Screen Using a Diverse Panel of Cultured Human Tumor Cell Lines", J Natl Cancer Inst, Jun. 5, 1991, 757-766, vol. 83, No. 11.

Rubinstein, L.V., "Comparison of In Vitro Anticancer-Drug-Screening Data Generated with a Tetrazolium Assay Versus a Protein Assay Against a Diverse Panel of Human Tumor Cell Lines", J Natl Cancer Inst, Jul. 4, 1990, 1113-1118, vol. 82, No. 13.

Skehan, P., "New Colorimetric Cytotoxicity Assay for Anticancer-Drug Screening", J Natl Cancer Inst, Jul. 4, 1990, 1107-1112, vol. 82, No. 13.

Rose, D.P., "Omega-3 fatty acids as cancer chemopreventive agents", Pharmacology & Therapeutics, 1999, 217-244, 83.

Ohta et al., "Action of a New Mammalian DNA Polymerase Inhibitor, Sulfoquinovosyldiacylglycerol", Biol. Pharm. Bull., 1999, 111-116, 22(2).

Pacetti et al., "High performance liquid chromatography-tandem mass spectrometry of phospholipid molecular species in eggs from hens fed diets enriched in seal blubber oil", Journal of Chromatography A, 2005, 66-73, 1097.

An abstract of Myrdal et al., "Solubilization of Drugs in Aqueous Media" Department of pharmacy Practice and Science, College of Pharmacy, The University of Arizona, Encyclopedia of pharmaceutical technology, published on Oct. 2, 2006.

An abstract of Rohan et al., "Dietary factors and survival from breast cancer", National Cancer Institute of Canada (NCIC) Epidemiology Unit, University of Toronto, Nutr Cancer 1993,20(2) 167-77.

Kafrawy et al., "Docosahexaenoic acid in phosphatidylcholine mediates cytotoxacity more effectively than other ω-3 and ω-6 fatty acids", Department of Biology, Indiana University, Cancer Letters 132(1998) 23-29.

Aggarwal et al., Chapter 10, Curcumin-Biologican and medicinal Properties, 2007, Medicinal and Aromatic Plants—Industrial Profiles, Turmeric, 45, 297-368.

Kawashima et al., "Inhibition of Rat Liver Microsomal Desaturases by Curcumin and Related Compounds", Biosci. Biotech. Biochem., 60(1), pp. 108-110, 1996.

Shimizu et al., "Sesamin Is a Potent and Specific Inhibitor of Δ5 Desaturase in Polyunsaturated Fatty Acid Biosynthesis", Lipids, vol. 26, No. 7, pp. 512-516, 1991.

Nakano et al., "Inhibitory Effects of Capsaicinoids on Fatty Acid Desaturation in a Rat Liver Cell Line", Biosci. Biotech. Biochem., 65(8), pp. 1859-1863, 2001.

Kawashima et al., "Nicardipine and Nifedipine Inhibit Fatty Acid Desaturases in Rat Liver Microsomes", Biosci. Biotech. Biochem., 60(10), pp. 1672-1676, 1996.

Kawashima et al., "Inhibitory effects of alkyl gallate and its derivatives on fatty acid desaturation", Biochimica et Biophysica Acta 1299, pp. 34-38, 1996.

Chau et al., "Monoglyceride and diglyceride lipases from human platelet microsomes", Biochimica et Biophysical Acta, 963, pp. 436-444, 1998.

* cited by examiner

POLYUNSATURATED FATTY ACID MONOGLYCERIDES, DERIVATIVES, AND USES THEREOF

CROSS-REFERENCE TO RELATED APPLICATIONS

The present application is a continuation-in-part of PCT international patent application No. PCT/CA2008/000301 filed on Feb. 14, 2008, which claims priority on U.S. provisional application No. 60/889,984 filed on Feb. 15, 2007. These applications are incorporated herein by reference in their entirety.

FIELD OF THE DISCLOSURE

The present document relates to the field of medicinal chemistry. More particularly it relates to the field of active agents used as cancer chemopreventive agent and radioenhencer for radiotherapy of cancer.

BACKGROUND OF THE DISCLOSURE

An estimated 153,100 new cases of cancer and 70,400 deaths from cancer will occur in Canada in 2006. Men outnumber women for both new cases and deaths, by 5% for incidence and 11% for mortality. Three types of cancer account for at least 55% of new cases in each sex: prostate, lung, and colorectal cancers in males, and breast, lung, and colorectal cancers in females. Twenty nine percent of cancer deaths in men and 26% in women are due to lung cancer alone. On the basis of current incidence rates, 38% of Canadian women and 44% of men will develop cancer during their lifetimes. On the basis of current mortality rates, 24% of women and 29% of men, or approximately 1 out of every 4 Canadians, will die from cancer (Canadian cancer society, 2006).

Over the past two decades the Division of Cancer Prevention of the US National Cancer Institute has organized a research and development program for the clinical evaluation of potential cancer preventive agents. The NCI define chemoprevention as an innovative area of cancer research that focuses on the prevention of cancer through pharmacologic, biologic, and nutritional interventions. As originally described, this involves the primary prevention of initiation and the secondary prevention, delay, or reversal of promotion and progression (Crowell J. A., and al., European Journal of Cancer 41, 2005).

Epidemiological studies have shown a correlation between high fat consumption and an increased risk of breast cancer (Wynder E L, Cancer, 58, 1986). In addition, both the type and amount of dietary fat appear to affect development of breast cancer (Bartsch H, and al. Carcinogenesis 20, 1999). A relatively high intake of n-6 polyunsaturated fatty acids (PUFAs) is considered to be a risk factor and is associated with a more advanced stage of the disease at the time of diagnosis (Nomura A M, and al., Breast Cancer Res Treat 18, 1991) and reduced survival (Rohan T E, and al., Nutr Cancer, 20, 1993). In contrast, an inverse relationship exists between the incidence of breast cancer and the level of fish consumption, suggesting a protective role for n-3 PUFAs in human breast cancer.

A diet containing LA (n-6 PUFA) stimulated the growth and metastasis of human breast cancer cells transplanted into athymic nude mice, whereas EPA or DHA exerted suppressive effects compared with palmitic acid (PA). Thus, in agreement with the epidemiological observations, LA (n-6 PUFA) accelerates, whereas EPA and DHA (n-3 PUFA) suppress mammary cancer compared with PA diet in experimental systems (Rose D P, and al., JNCI 87, 1995) (Senzaki H, and al., Anticancer Res 18, 1998).

SUMMARY OF THE DISCLOSURE

According to one aspect there are provided compounds of formulas (I), (II), (III), and (IV):

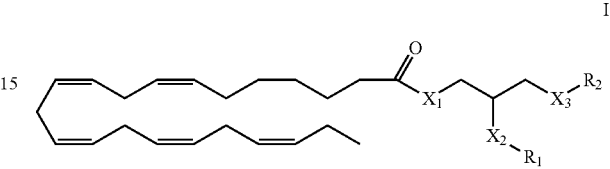

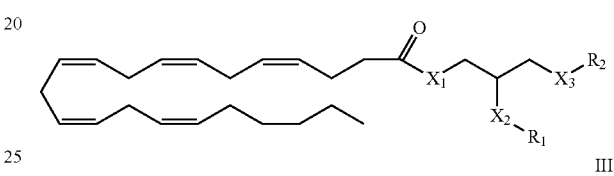

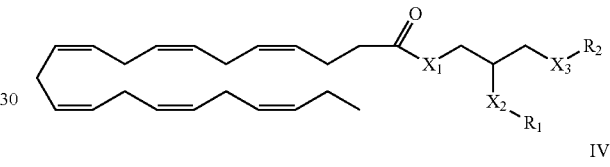

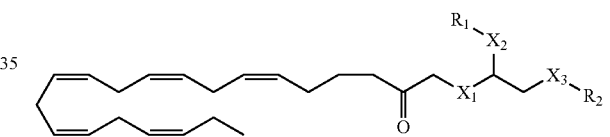

wherein
$X_1$ is O, NH, or S;
$X_2$ is O, NH, or S;
$X_3$ is O, NH, or S;
$R_1$ and $R_2$ each independently represents —H, —C(O)NH$_2$, —S(O)NH$_2$, —S(O)$_2$NH$_2$, —C1-C22 (oxy)alkyl, —C1-C22 alkyl, —C1-C22 (hydroxy)alkyl, —C1-C22 (amino)alkyl, —C1-C22 (halo)alkyl, —C3-C22 alkenyl, —C3-C22 alkynyl, —(C3-C7) cycloalkyl unsubstituted or substituted with at least one substituent chosen from C1-C22 alkyl, —C2-C22 alkenyl, and —C2-C22 alkynyl, —C6-C12 aryl, —C7-C22 (aryl)alkyl, —C8-C22 (aryl)alkenyl, —C8-C22 (aryl)alkynyl, three- to seven-membered non-aromatic heterocycle unsubstituted or substituted with at least one substituent chosen from —C1-C22 alkyl, —C2-C22 alkenyl, and —C2-C22 alkynyl, five- to seven-membered aromatic heterocycle unsubstituted or substituted with at least one substituent chosen from —C1-C22 alkyl, —C2-C22 alkenyl, and —C2-C22 alkynyl, —(CH$_2$)$_n$ amino acid wherein the amino acid is connected through its alpha carbon atom, —(CH$_2$)$_n$ peptide wherein the peptide is connected through the alpha carbon atom of one of its amino acids, —CH$_2$OR$_5$, —C(O)R$_5$, —C(O)OR$_5$, —C(O)NR$_5$, —P(O)(OR$_5$)$_2$, —S(O)$_2$NHR$_5$, —SOR$_5$, —S(O)$_2$R$_5$, -arylP(O)(OR$_5$)$_2$, a sugar, or a sugar phosphate or R₁ and R₂ are joined together so as to form a five- to seven-membered non-aromatic heterocycle unsubstituted or substituted with at least one substituent chosen from —C1-C22 alkyl, —C2-C22 alkenyl, and —C2-C22 alkynyl, a phosphate, sulfate carbonyl group, or a thiocarbonyl imine;

R₅ is —H, —C1-C22 alkyl, —(C3-C7) cycloalkyl, —C1-C22 (halo)alkyl, —C6-C12 aryl, —C2-C22 alkenyl, —C2-C22 alkynyl, —C7-C22 (aryl)alkyl, —C8-C22 (aryl)alkenyl, —C8-C22 (aryl)alkynyl, —C1-C22 (hydroxy)alkyl, —C1-C22 alkoxy, —C1-C22 (amino)alkyl, a —(C3-C7) cycloalkyl unsubstituted or substituted with at least one substituent chosen from —C1-C22 alkyl, —C2-C22 alkenyl, and —C2-C22 alkynyl, a three- to seven-membered non-aromatic heterocycle unsubstituted or substituted at least one substituent chosen from —C1-C22 alkyl, —C2-C22 alkenyl, and —C2-C22 alkynyl, a three- to seven-membered aromatic heterocycle unsubstituted or substituted with at least one substituent chosen from —C1-C22 alkyl, —C2-C22 alkenyl, and —C2-C22 alkynyl, a —(CH₂)ₙ amino acid wherein the amino acid is connected to the compound through its alpha carbon atom, a —(CH₂)ₙ peptide wherein the peptide is connected to the compound through the alpha carbon atom of one of its amino acids, a sugar or a sugar phosphate; and n is an integer having a value of 0, 1, 2, 3, or 4, and pharmaceutically acceptable salts thereof.

According to another aspect there are provided compounds of formulas (V), (VI), (VII), (VIII), (IX), (X), (XI), (XII), (XIII), (XIV) or (XV):

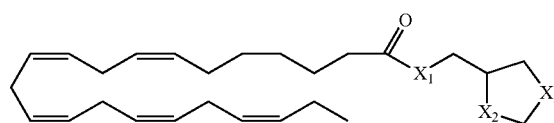

V

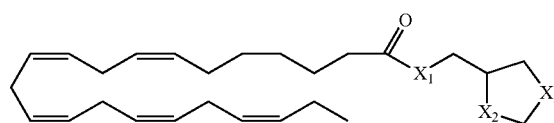

VI

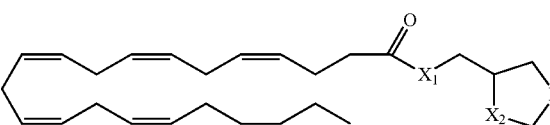

VII

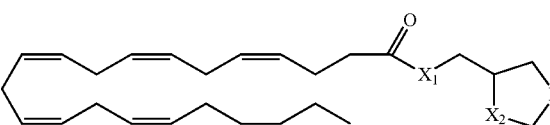

VIII

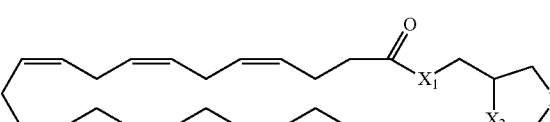

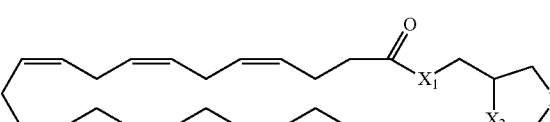

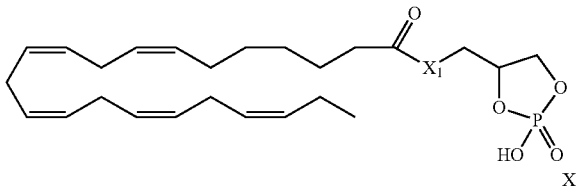

IX

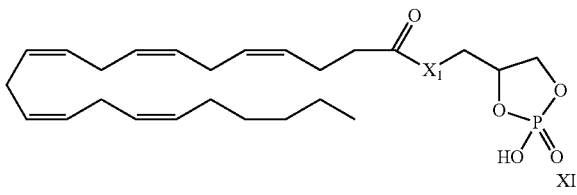

X

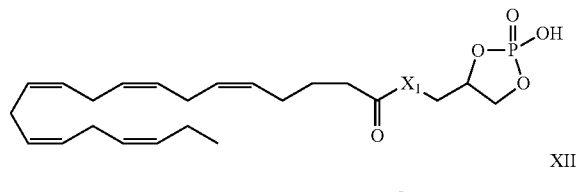

XI

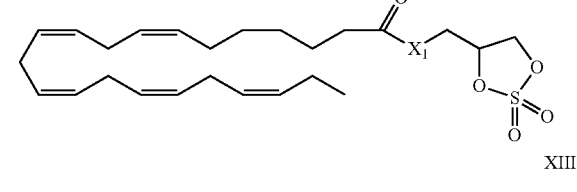

XII

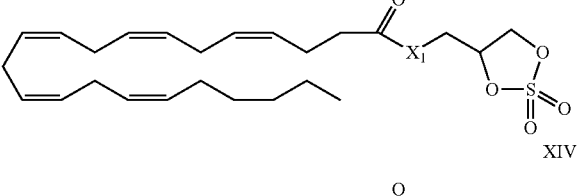

XIII

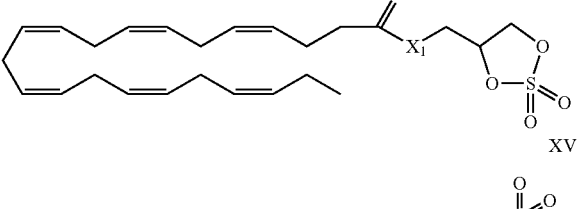

XIV

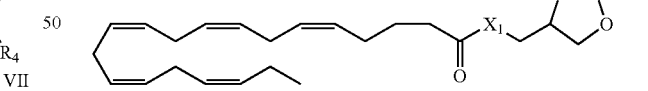

XV

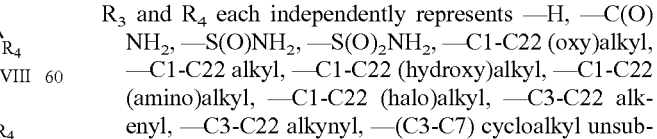

$X_1$ is O, NH, or S;
$X_2$ is O, NH, or S;
$X_3$ is O, NH, or S;
$R_3$ and $R_4$ each independently represents —H, —C(O)NH₂, —S(O)NH₂, —S(O)₂NH₂, —C1-C22 (oxy)alkyl, —C1-C22 alkyl, —C1-C22 (hydroxy)alkyl, —C1-C22 (amino)alkyl, —C1-C22 (halo)alkyl, —C3-C22 alkenyl, —C3-C22 alkynyl, —(C3-C7) cycloalkyl unsubstituted or substituted with at least one substituent chosen from C1-C22 alkyl, —C2-C22 alkenyl, and —C2-C22 alkynyl, —C6-C12 aryl, —C7-C22 (aryl)alkyl, —C8-C22 (aryl)alkenyl, —C8-C22 (aryl)alkynyl, three- to seven-membered non-aromatic heterocycle unsubstituted or substituted with at least one substituent chosen from —C1-C22 alkyl, —C2-C22 alkenyl, and —C2-C22 alkynyl, five- to seven-membered aromatic heterocycle unsubstituted or substituted with at least one substituent chosen from —C1-C22 alkyl, —C2-C22 alkenyl, and —C2-C22 alkynyl, —(CH$_2$)$_n$ amino acid wherein the amino acid is connected through its alpha carbon atom, —(CH$_2$)$_n$ peptide wherein the peptide is connected through the alpha carbon atom of one of its amino acids, —CH$_2$OR$_5$, —C(O)R$_4$, —C(O)OR$_4$, —C(O)NR$_4$, —P(O)(OR$_5$)$_2$, —S(O)$_2$NHR$_5$, —SOR$_5$, —S(O)$_2$R$_5$, -arylP(O)(OR$_5$)$_2$, a sugar, or a sugar phosphate, or R$_3$ and R$_4$ are joined together so as to form a five- to seven-membered non-aromatic heterocycle unsubstituted or substituted with at least one substituent chosen from —C1-C22 alkyl, —C2-C22 alkenyl, and —C2-C22 alkynyl, a phosphate, sulfate carbonyl group, or a thiocarbonyl imine;

R$_5$ is —H, —C1-C22 alkyl, —(C3-C7) cycloalkyl, —C1-C22 (halo)alkyl, —C6-C12 aryl, —C2-C22 alkenyl, —C2-C22 alkynyl, —C7-C22 (aryl)alkyl, —C8-C22 (aryl)alkenyl, —C8-C22 (aryl)alkynyl, —C1-C22 (hydroxy)alkyl, —C1-C22 alkoxy, —C1-C22 (amino) alkyl, a —(C3-C7) cycloalkyl unsubstituted or substituted with at least one substituent chosen from —C1-C22 alkyl, —C2-C22 alkenyl, and —C2-C22 alkynyl, a three- to seven-membered non-aromatic heterocycle unsubstituted or substituted at least one substituent chosen from —C1-C22 alkyl, —C2-C22 alkenyl, and —C2-C22 alkynyl, a three- to seven-membered aromatic heterocycle unsubstituted or substituted with at least one substituent chosen from —C1-C22 alkyl, —C2-C22 alkenyl, and —C2-C22 alkynyl, a —(CH$_2$)$_n$ amino acid wherein the amino acid is connected to the compound through its alpha carbon atom, a —(CH$_2$)$_n$ peptide wherein the peptide is connected to the compound through the alpha carbon atom of one of its amino acids, a sugar or a sugar phosphate; and n is an integer having a value of 0, 1, 2, 3, or 4;

and pharmaceutically acceptable salts thereof.

It was found that such compounds can be used so as to reduce or inhibit tumor growth, or inhibit tumor cell proliferation in vitro as well as in vivo. It was also found that the compounds previously mentioned can be useful as cancer chemopreventive agents (for example breast cancer, prostate cancer, colon cancer and lung cancer). The compounds of the present disclosure can be used separately or in a mixture of at least two of them (for example 2, 3 or 4 of them). The compounds of the present disclosure can also be in isolated form. The compounds of the present disclosure can be used as a composition which also includes a pharmaceutically acceptable carrier.

It was also found that the compounds previously mentioned can provide effective pharmaceutical compositions for chemoprevention of cancer. Such compositions can comprise at least two compounds chosen from compounds of formulas (I), (II), (III), and (IV).

The compounds and compositions of the present disclosure can also be effective as radioenhencers for radiotherapy of cancer, or in combination with a pharmaceutically active ingredient in chemotherapy of cancer.

The compounds and compositions of the present disclosure can be effective for chemoprevention of various types of cancers (such as breast cancer, lung cancer, prostate cancer, colon cancer). Tumors growth of such types of cancer can be inhibited or reduced with these compounds.

The compounds and compositions of the present disclosure can be used for treating cancer (for example breast cancer, lung cancer, prostate cancer, colon cancer).

According to another aspect there is provided a method for chemopreventing cancer comprising the step of administering to a subject an effective amount of at least one compound chosen from compounds of formulas (I), (II), (III), (IV), (V), (VI), (VII), (VII), (IX), (X), (XI), (XII), (XIII), (XIV) and (XV).

According to another aspect there is provided a method for inhibiting tumor growth, inhibiting tumor cell proliferation, or reducing tumor growth, in vitro or in vivo, comprising contacting the tumor with an effective amount of a at least one compound chosen from compounds of formulas (I), (II), (III), (IV), (V), (VI), (VII), (VII), (IX), (X), (XI), (XII), (XIII), (XIV) and (XV).

According to another aspect there is provided a method of reducing tumor growth in a subject comprising administering to the subject an effective amount of at least one compound chosen from compounds of formulas (I), (II), (III), (IV), (V), (VI), (VII), (VII), (IX), (X), (XI), (XII), (XIII), (XIV) and (XV).

According to another aspect there is provided a method for treating cancer (for example breast cancer, lung cancer, prostate cancer, colon cancer) comprising administering to the subject in need thereof an effective amount of at least one compound chosen from compounds of formulas (I), (II), (III), (IV), (V), (VI), (VII), (VIII), (IX), (X), (XI), (XII), (XIII), (XIV) and (XV).

BRIEF DESCRIPTION OF THE FIGURES

Further features and advantages of the disclosure will become more readily apparent from the following description of specific embodiments as illustrated by way of examples in the appended figures wherein.

DETAILED DESCRIPTION OF THE DISCLOSURE

Figure 1:
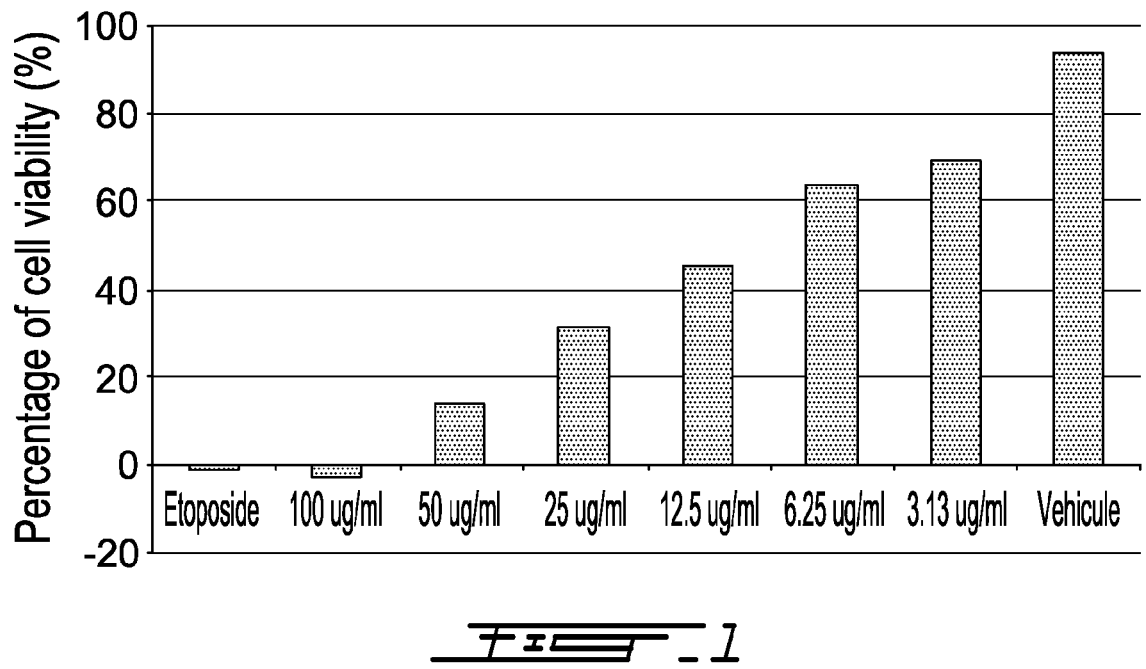
FIG. 1 is a diagram showing the results of an in vitro assay of a composition according to an embodiment of the present disclosure, wherein the assay was carried out on A549 human cancer cell line.

Further features and advantages of the previously-mentioned compounds will become more readily apparent from the following description of non-limiting examples.

According to another aspect there is provided a method for preparing a compound of formula (V), (VI), (VII), (VIII), (IX), (X), (XI), (XII), (XIII), (XIV) or (XV), the method comprising reacting a compound of formula (XVI), (XVII), or (XVIII)

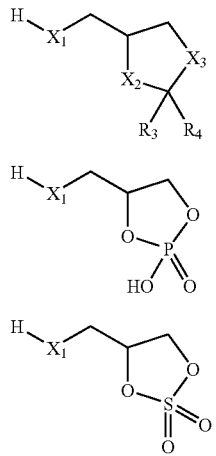

in which $X_1$, $X_2$, $X_3$, $R_3$ and $R_4$ are as previously defined, with at least one ester of at least one fatty acid chosen from

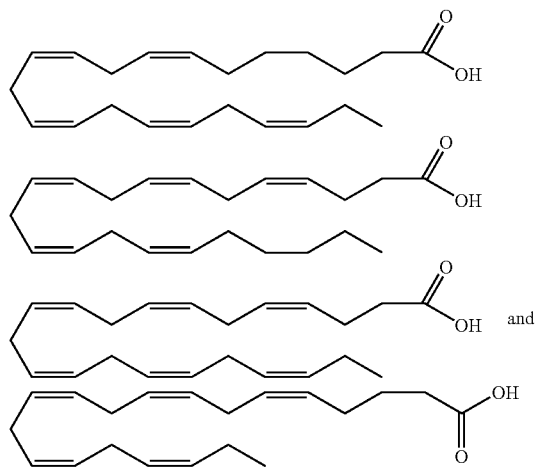

being understood that when a compound of formula (XVI) is used, a compound of formula (V), (VI), (VII), or (VIII) is obtained, when a compound of formula (XVII) is used, a compound of formula (IX), (X), or (XI) is obtained, and when a compound of formula (XVIII) is used, a compound of formula (XII), (XIII), (XIV) or (XV) is obtained.

For example, a compound of formula (XVI) and the fatty acid ester can be reacted together in the presence of a base (such as KOH or NaOH). Alternatively, they can be reacted together in the presence of an enzyme for example a lipase such as *Candida antartica*.

The method can further comprises treating the obtained compound of formula (V), (VI), (VII), or (VII) under acidic conditions so as to open its heterocycle ring and protonate $X_2$ and $X_3$.

For example, the compound of formula (XVI) can be

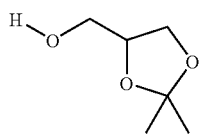

The method can further comprise treating the obtained compound of formula (V), (VI), (VII), or (VIII) under acidic conditions so as to obtain

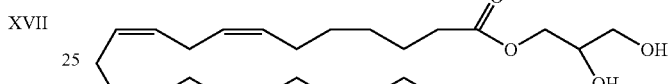

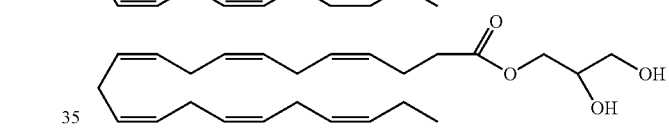

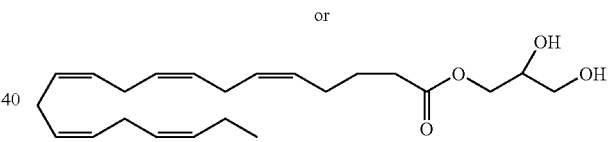

or

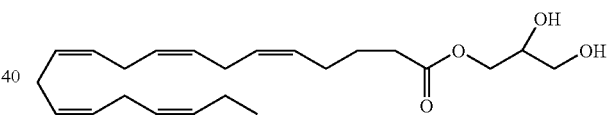

The acidic conditions can be brought by an acid chosen from acetic acid, formic acid, hydrochloric acid, p-toluenesulfonic acid, trifluoroacetic acid, perchloric acid and pyridinium tosylate or by an acidic resin.

The ester can be C1-C6 alkyl ester of the fatty acid. Alternatively the ester can be a monoglyceride or a diglyceride in which at least one of the oxygen atom of the glycerol backbone forms an ester with the fatty acid. The ester can also be a triglyceride in which the three oxygen atoms of the glycerol backbone form an ester with one molecule of the fatty acid.

The ester can also be a diglyceride or triglyceride in which at least one oxygen atoms of the glycerol backbone forms an ester with another omega-3 fatty acid or another omega-6 fatty acid.

For example, preparation of compounds of formulas (V), (VI), (VII), (VIII), (IX), (X), (XI), (XII), (XIII), (XIV) and (XV) can be carried out by reacting together a fish oil which contains the triglyceride with the compound of formula (V), (VI), (VII), (VIII), (IX), (X), (XI), (XII), (XIII), (XIV) or (XV).

In fact, various oils rich in omega-3 and/or omega-6 fatty acids can be used. For example, vegetal oils (such as flaxseed oil, pumpkinseed oil, canola oil, soybean oil, walnut oil, etc.) and marine oils (such as algae oil, seal oil, krill oil, fish oil (for example cod liver oil, salmon oil, tuna oil, shark oil, pelagic fishes oil, sardine oil, etc)) can be used.

The method can comprise reacting the compound of formula (XVI), (XVII), or (XVIII) with at least two different fatty acids chosen from the fatty acids previously defined. The method can also comprise reacting more than one compound chosen from the compounds of formulas (XVI), (XVII), and (XVIII).

The term "aryl" as used herein refers to a cyclic or polycyclic aromatic ring. For example, the aryl group can be phenyl or napthyl.

The expression "aromatic heterocycle" as used herein refers to an aromatic cyclic or fused polycyclic ring system having at least one heteroatom selected from the group consisting of N, O, S and P. Non-limitative examples include heteroaryl groups are furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl, quinazolinyl, and so on.

The expression "non-aromatic heterocycle" includes non-aromatic rings or ring systems that contain at least one ring having at least one hetero atom (such as nitrogen, oxygen, sulfur or phosphorus). This term includes, in a non-limitative manner all of the fully saturated and partially unsaturated derivatives of the above mentioned aromatic heterocycles groups. Examples of non-aromatic heterocycle groups include, in a non-limitative manner, pyrrolidinyl, tetrahydrofuranyl, morpholinyl, thiomorpholinyl, piperidinyl, piperazinyl, thiazolidinyl, isothiazolidinyl, and imidazolidinyl.

The expression "inflammatory disease(s)" as used herein refers to all of the acute or chronic inflammatory diseases associated with the excessive release of cytokines, and complication thereof. The expression "chronic inflammatory disease(s)" refers to all diseases that induce tissue injury or induce continuous inflammation due to hyperactivity and the excessive release of cytokines, and complication thereof. In particular, the inflammatory diseases to which the compounds and compositions of the present disclosure can be applied are not limited to, but include inflammatory bowel disease such as Crohn's disease and ulcerative colitis, peritonitis, osteomyelitis, cellulitis, meningitis, cerebritis, pancreatitis, trauma-inducing shock, bronchial asthma, allergic rhinitis, cystic fibrosis, cerebral apoplexy, acute bronchitis, chronic bronchitis, acute bronchiolitis, chronic bronchiolitis, osteoarthritis, gout, spinal arthropathy, ankylosing spondylitis, Reiter's syndrome, psoriatic arthropathy, enteropathic spondylitis, juvenile arthropathy, juvenile ankylosing spondylitis, reactive arthropathy, infectious arthritis, post-infectious arthritis, gonococcal arthritis, tuberculous arthritis, viral arthritis, fungal arthritis, syphilitic arthritis, Lyme disease, arthritis associated with 'vasculitis syndrome', polyarteritis nodosa, hypersensitivity vasculitis, Wegener's granulomatosis, polymyalgia rheumatica, giant cell arteritis, calcium crystal deposition arthropathy, pseudogout, non-joint rheumatism, bursitis, tenosynovitis, epicondylitis (tennis elbow), neuropathic joint disease (charcot joint), hemarthrosic, Henoch-Schonlein purpura, hypertrophic osteoarthropathy, multicentric reticulohistiocytoma, scoliosis, hemochromoatosis, meniscocytosis, other hemoglobinopathy, hyperlipoproteinemia, hypogammaglobulinaemia, familial Mediterranean fever, Gerhardt Disease, systemic lupus erythematosus, relapsing fever, psoriasis, multiple sclerosis, sepsis (septicemia), septic shock, acute respiratory distress syndrome, multiple organ dysfunction syndrome, chronic obstructive pulmonary disease, rheumatic arthritis, acute lung injury, bronchopulmonary dysplasia and so on.

The expression "effective amount" of a compound of the present disclosure or of a composition of the present disclosure is a quantity sufficient to, when administered to the subject, including a mammal, for example a human, effect beneficial or desired results, including clinical results, and, as such, an "effective amount" or synonym thereto depends upon the context in which it is being applied. For example, in the context of treating cancer, for example, it is an amount of the compound sufficient to achieve such treatment of the cancer as compared to the response obtained without administration of the compound. The amount of a given compound of the present disclosure that will correspond to an effective amount will vary depending upon various factors, such as the given drug or compound, the pharmaceutical formulation, the route of administration, the type of disease or disorder, the identity of the subject or host being treated, and the like, but can nevertheless be routinely determined by one skilled in the art. Also, as used herein, an "effective amount" of a compound of the present disclosure is an amount which inhibits, suppresses or reduces a cancer (e.g., as determined by clinical symptoms or the amount of cancerous cells) in a subject as compared to a control. The same definition of "effective amount" also applies when the compounds of the present disclosure are used for inhibiting tumor growth, inhibiting tumor cell proliferation, or reducing tumor growth.

The term "subject" as used herein includes all members of the animal kingdom including human. According to one embodiment, the subject is a human.

The expression "pharmaceutically acceptable" means compatible with the treatment of subjects such as animals or humans.

The expression "pharmaceutically acceptable salt" means an acid addition salt or basic addition salt which is suitable for or compatible with the treatment of subjects such as animals or humans.

The expression "pharmaceutically acceptable acid addition salt" as used herein means any non-toxic organic or inorganic salt of any compound of the present disclosure, or any of its intermediates. Illustrative inorganic acids which form suitable salts include hydrochloric, hydrobromic, sulfuric and phosphoric acids, as well as metal salts such as sodium monohydrogen orthophosphate and potassium hydrogen sulfate. Illustrative organic acids that form suitable salts include mono-, di-, and tricarboxylic acids such as glycolic, lactic, pyruvic, malonic, succinic, glutaric, fumaric, malic, tartaric, citric, ascorbic, maleic, benzoic, phenylacetic, cinnamic and salicylic acids, as well as sulfonic acids such as p-toluene sulfonic and methanesulfonic acids. Either the mono or di-acid salts can be formed, and such salts may exist in either a hydrated, solvated or substantially anhydrous form. In general, the acid addition salts of the compounds of the present disclosure are more soluble in water and various hydrophilic organic solvents, and generally demonstrate higher melting points in comparison to their free base forms. The selection of the appropriate salt will be known to one skilled in the art. Other non-pharmaceutically acceptable salts, e.g. oxalates, may be used, for example, in the isolation of the compounds of the present disclosure, for laboratory use, or for subsequent conversion to a pharmaceutically acceptable acid addition salt. In embodiments of the present disclosure, the pharmaceutically acceptable acid addition salt is the hydrochloride salt.

The term "pharmaceutically acceptable basic addition salt" as used herein means any non-toxic organic or inorganic base addition salt of any acid compound of the disclosure, or any of its intermediates. Acidic compounds of the disclosure that may form a basic addition salt include, for example, where R is $CO_2H$. Illustrative inorganic bases which form suitable salts include lithium, sodium, potassium, calcium, magnesium or barium hydroxide. Illustrative organic bases which form suitable salts include aliphatic, alicyclic or aromatic organic amines such as methylamine, trimethylamine and picoline or ammonia. The selection of the appropriate salt will be known to a person skilled in the art. Other non-pharmaceutically acceptable basic addition salts, may be used, for example, in the isolation of the compounds of the disclosure, for laboratory use, or for subsequent conversion to a pharmaceutically acceptable acid addition salt.

The formation of a desired compound salt is achieved using standard techniques. For example, the neutral compound is treated with an acid or base in a suitable solvent and the formed salt is isolated by filtration, extraction or any other suitable method.

The expression "lipophilic active agent" as used herein refers to an active agent which has an affinity for, or capability of dissolving in, lipids; i.e., non-water soluble oils, fats, sterols, triglycerides and the like.

The term "lipid" as used herein refers to a synthetic or naturally-occurring amphipathic compound which comprises a hydrophilic component and a hydrophobic component. Lipids include, for example, fatty acids, neutral fats, phosphatides, glycolipids, aliphatic alcohols and waxes, terpenes and steroids.

The expression "fatty acid(s)" as used herein refers to long chain aliphatic acids (alkanoic acids) of varying chain lengths, from about C12 to C22 (although both longer and shorter chain-length acids are known). For example, the predominant chain lengths are about C16 to about C22. The structure of a fatty acid is represented by a simple notation system of "X:Y", where X is the total number of carbon (C) atoms and Y is the number of double bonds.

Generally, fatty acids are classified as saturated or unsaturated. The term "saturated fatty acids" refers to those fatty acids that have no "double bonds" between their carbon backbone. In contrast, "unsaturated fatty acids" are cis-isomers that have "double bonds" along their carbon backbones. "Monounsaturated fatty acids" have only one "double bond" along the carbon backbone (e.g., usually between the 9th and 10th carbon atom as for palmitoleic acid (16:1) and oleic acid (18:1)), while "polyunsaturated fatty acids" (or "PUFAs") have at least two double bonds along the carbon backbone (e.g., between the 9th and 10th, and 12th and 13th carbon atoms for linoleic acid (18:2); and between the 9th and 10th, 12th and 13th, and 15th and 16th for [alpha]-linolenic acid (18:3)).

"PUFAs" can be classified into two major families (depending on the position (n) of the first double bond nearest the methyl end of the fatty acid carbon chain). Thus, the "[omega]-6 fatty acids" [omega]-6 or n-6) have the first unsaturated double bond six carbon atoms from the omega (methyl) end of the molecule and additionally have a total of two or more double bonds, with each subsequent unsaturation occurring 3 additional carbon atoms toward the carboxyl end of the molecule. In contrast, the "[omega]-3 fatty acids" ([omega]-3 or n-3) have the first unsaturated double bond three carbon atoms away from the omega end of the molecule and additionally have a total of three or more double bonds, with each subsequent unsaturation occurring 3 additional carbon atoms toward the carboxyl end of the molecule.

Compounds of the present disclosure include radiolabeled forms, for example, compounds labeled by incorporation within the structure $^2H$, $^3H$, $^{14}C$, $^{15}N$, or a radioactive halogen such as $^{125}I$. A radiolabeled compound of the compounds of the present disclosure may be prepared using standard methods known in the art.

As used herein, and as well understood in the art, "treatment" or "treating" is an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treatment" or "treating" can also mean prolonging survival as compared to expected survival if not receiving treatment.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives.

The sugar can be chosen from 5-carbon sugars and 6-carbon sugars. Non-limiting examples of 5-carbon sugar include ribose, arabinose, xylose, and lyxose. Non-limiting examples of 6-carbon sugar include glucose, galactose, mannose, allose, gulose, idose, talose, and altrose.

The sugar phosphate can be chosen from monosaccharides (such as mannose-6-phosphate, glucose-6-phosphate, galactose-6-phosphate, mannose-l-phosphate, glucose-l-phosphate and galactose-l-phosphate), disaccharides (such as 6-O-phosphoryl-a-D-mannopyranosyl-(1-2)-D-mannopyranose, 6-O-phosphoryl-a-D-mannopyranosyl-(1-3)-mannopyranose, 6-O-phosphoryl-a-D-mannopyranosyl-(1-6)-D-mannopyranose), trisaccharides (such as 6-O-phosphoryl-a-D-mannopyranosyl-(1-2)-D-mannopyranosyl-(l-2)-D-mannopyranose), and higher linear or branched oligosaccharides (such as pentamannose-6-phosphate).

The amino acid can be chosen from alanine, arginine, asparagine, aspartic acid, cysteine, glutamine, glutamic acid, glycine, isoleucine, leucine, lysine, methionine, phenylalanine, proline, serine, threonine, tryptophan, tyrosine, and valine.

The peptide can be chosen from any possible combination of the amino acids previously described.

For example, the compounds of the present disclosure can be of formulas:

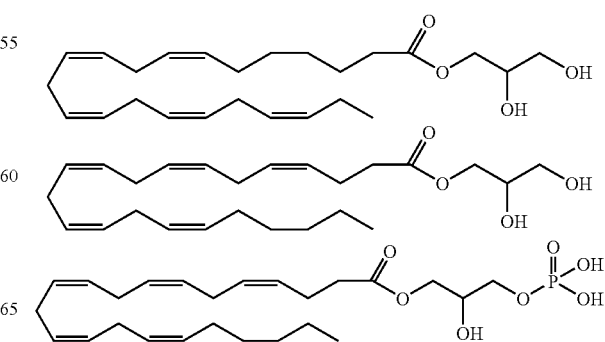

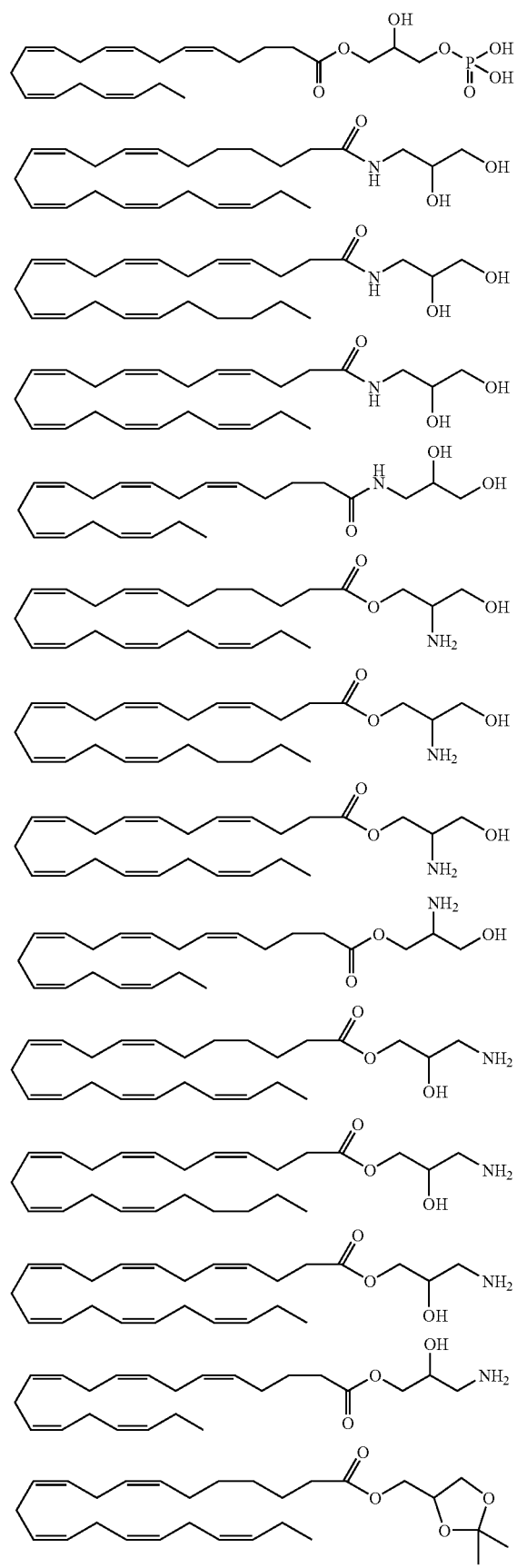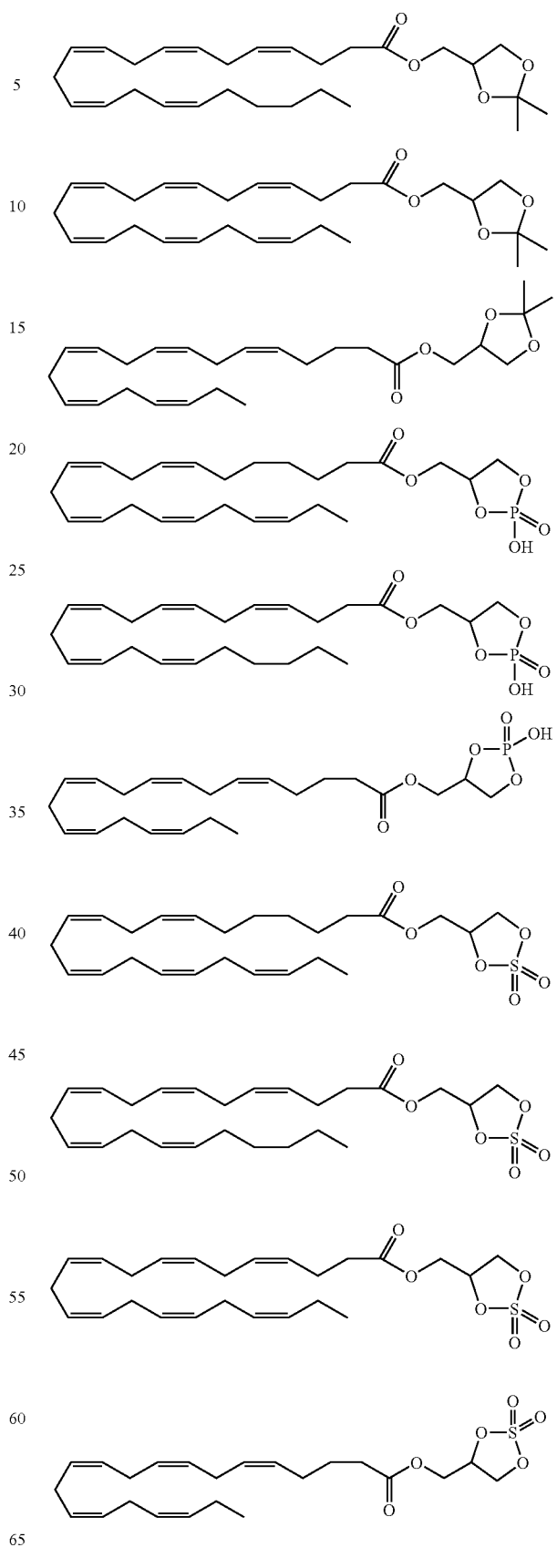

Example 1

Preparation of Monoglyceride 1

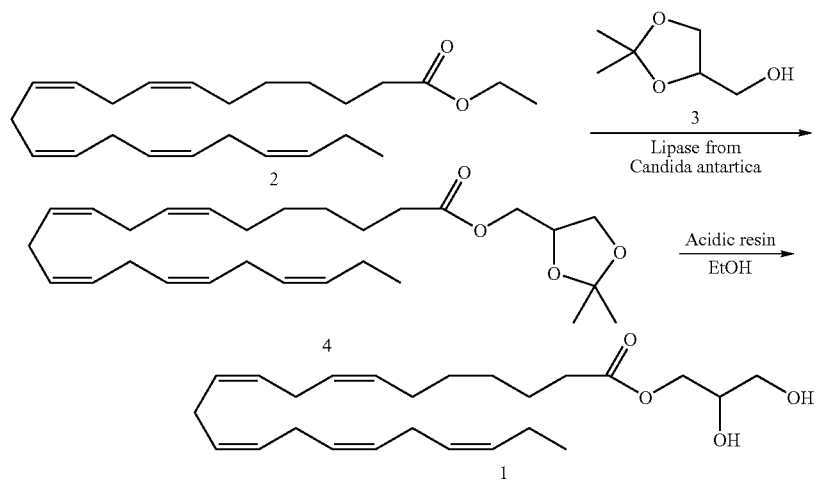

Docosapentaenoic acid ethyl ester (compound 2) (10 g) and compound 3 (6 g) were mixed together and heated at a temperature of 60° C. The enzyme (100 mg) was added and the reaction mixture was stirred at 60° C. under vacuum (18 mbar) or under nitrogen bubbling for 5 h. The reaction mixture was filtered and the enzyme was washed with ethanol 95% (20 ml). The acidic resin (500 mg) or organic acid was added to the ethanol solution and heated to reflux for 18 h. The resin was removed by filtration and the ethanol was evaporated in vacuo. The resulting crude product was dissolved in a mixture of hexanes/ethyl acetate 90:10 (10 ml) and silica gel (40 g) was added. The slurry was put on a fritted funnel and eluted with hexanes/ethyl acetate 90:10 (150 ml) to remove unreacted starting material. A second elution with ethyl acetate (300 ml) give, after evaporation in vacuo, the pure compound 1 (8.7 g) was tested in vitro on the cell viability assay and in an in vivo xenograft tumor model.

Pure compounds 5 and 6 (see below) have also been successfully prepared by following the same procedure.

Example 2

Preparation of a Composition (Composition 1) Comprising Various Monoglycerides (Compounds 1, 5 and 6)

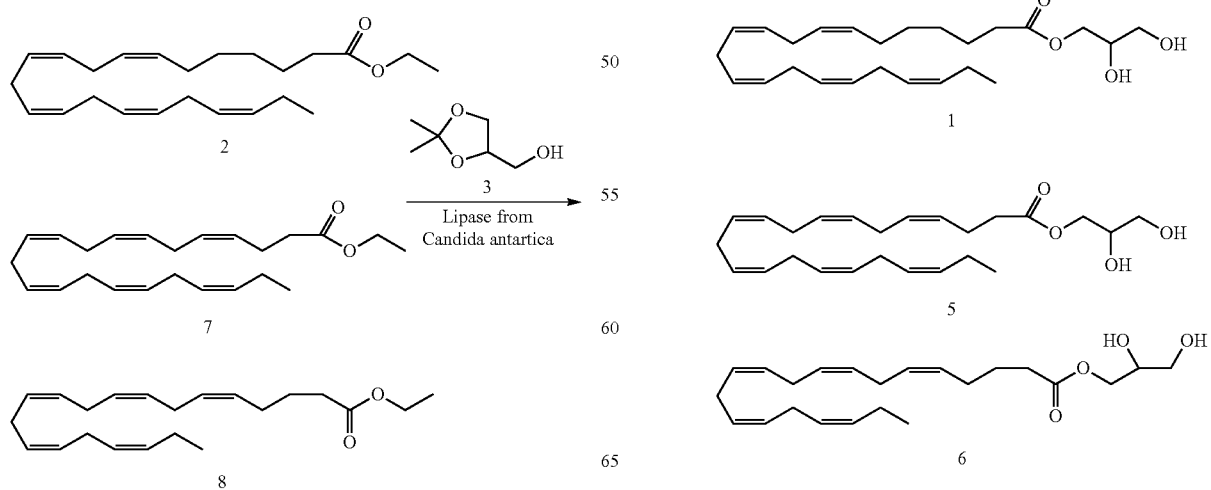

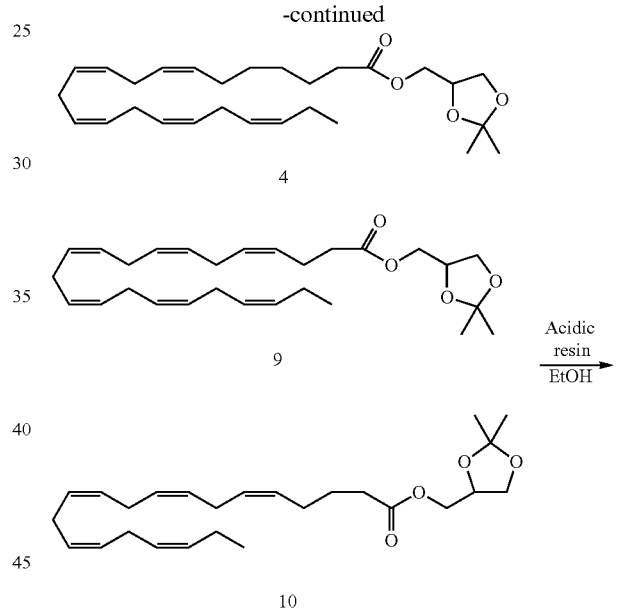

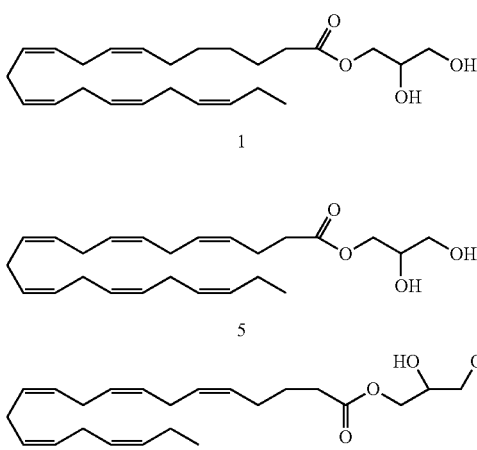

Composition 1 comprising compounds 1, 5 and 6 was prepared according to the same procedure as previously described in Example 1. The starting material was a mixture of compounds 2, 7, and 8 at respectively (10%, 80%, and 10%). This starting material composition was sold by the Company CRODA™ Chemical Europe Ltd. under the name INCROMEGA™ DHA 700 E SR. Thus, the obtained composition 1 contains 10% of compound 1, 80% of compound 5, and 10% of compound 6.

Example 3

Preparation of Monoglyceride 1

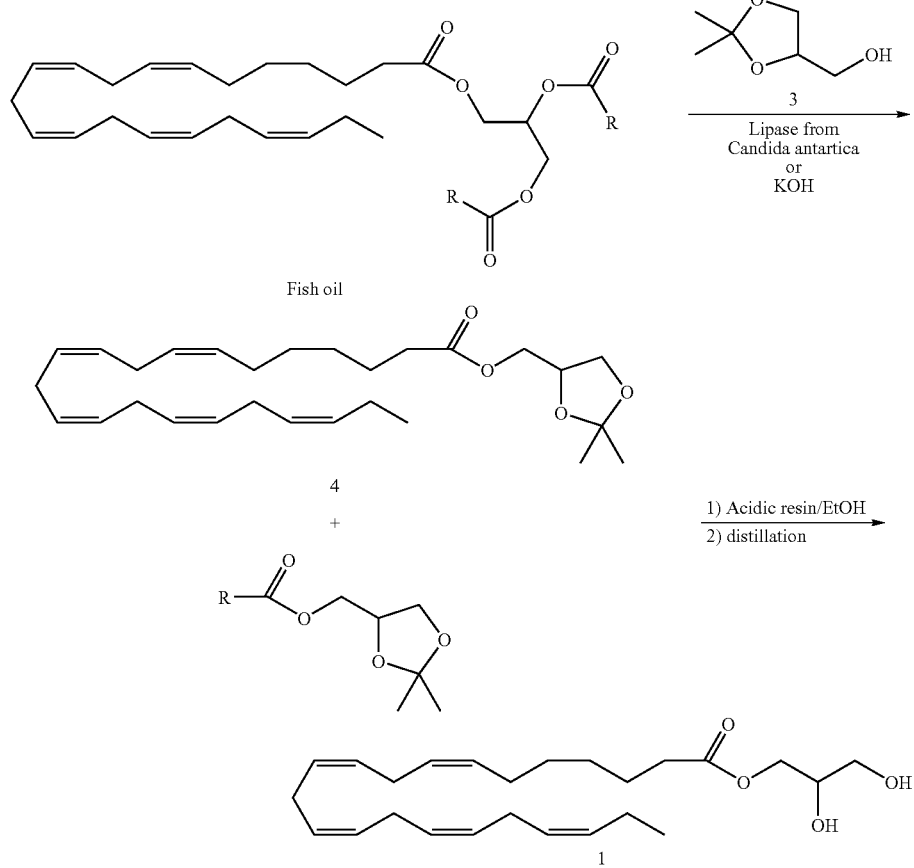

A fish oil (comprising pelagic fishes oil) (30 g) and compound 3 (6 g) were mixed together and heated at a temperature of 60° C. As illustrated in the above reaction scheme the fish oil can comprise a plurality of triglycerides. The two R groups, which can be the same or different, can represent the chain of various fatty acids or other organic acids present in such an oil. In such triglycerides, at least one oxygen atom of the glycerol backbone forms an ester with an omega-3 fatty acids. The enzyme (lipase) (100 mg) or KOH (1000 mg) was added and the reaction mixture was stirred at 60° C. for 3 h. The reaction mixture was filtered on a silica gel pad and the enzyme was washed with ethanol 95% (20 ml). The acidic resin (500 mg) or an acid was added to the ethanol solution and heated to reflux for 18 h. The resin was removed by filtration and the ethanol was evaporated in vacuo. The resulting crude product was distillated under reduced pressure to give the pure compound 1.

Various other oils rich in omega-3 and/or omega-6 fatty acids can be used. For example, vegetal oils (such as flaxseed oil, pumpkinseed oil, canola oil, soybean oil, walnut oil) and marine oils (such as algae oil, microalgae oil, phytoplankton oil, seal oil, krill oil, fish oil (for example cod liver oil, salmon oil, tuna oil, shark oil, sardine oil, etc)) can be used.

Example 4

The cell viability assay is performed to measure the relative cell viability status of cancer cells upon exposure to test compounds in comparison to a positive control (etoposide) and a negative control (vehicule). Adherent cells growing in 96-well plates are exposed to test compounds for 3 days (72 hours). Four cancer cell lines including lung, colon, prostate and breast types are used since these types of cancer possess high incidence in human. Test compounds (composition 1 comprising compounds 1, 5 and 6) as well as positive and negative controls were tested in parallel on the same culture plate. All conditions are tested in triplicate. Apoptotic agents such as etoposide or epigallo-catechin-gallate are used as positive controls to kill cells whereas the solvent (dimethyl-sulfoxide and water) is used as negative controls for basal determination. Inhibition of 50% of cell growth compared to basal condition is the lower limit indicating a positive biological response (considered as a hit). After the incubation time, total protein content is quantified following staining with the anionic dye sulforhodamine B (SRB). The detection of luminescence, emitted by SRB, is completed by a microplate reader. This method of detection is based upon works published by Monks et al., in Journal of the National Cancer Institute vol. 82 no. 13 (1991) p. 757, Skehan et al. in Journal of the National Cancer Institute vol. 82 no. 13 (1990) p. 1107 and Rubinstein et al. in Journal of the National Cancer Institute vol. 82 no. 13 (1990) p. 1113. The amount of luminescence is directly proportional to the number of living cells in culture.

Cancer cells were grown in T-75 flask (Falcon) containing 20 ml of appropriate culture medium, subcultured twice a week at 37° C., 5% $CO_2$, 95% air and 100% relative humidity and maintained at low passage number (5 to 20), following manufacturer recommendations. The cell lines used were A-549 (human lung carcinoma), HCT-15 (human colon adenocarcinoma), BT-549 (human breast ductal carcinoma) and PC3 (human prostate adenocarcinoma). Cells were trypsinized using 0.25% trypsine (w/v)/0.53 mM EDTA solution (Hyclone), counted and plated at densities between 1000 and 3000 cells per well in flat bottom 96-well clear plates (Becton Dickinson) in 100 µl of appropriate culture medium supplemented with fetal bovine serum (Hyclone). Culture plates were incubated at 37° C., 5% $CO_2$, 95% air and 100% relative humidity for 72 hours. At 20-30% of cell confluence, 80 µl of appropriate culture medium was added to each well. 20 µl of either a solution of test compounds in 6 different concentration, drug for positive controls (at concentration of 29 mg/ml) or solvent (vehicle or water) for negative controls were added on top of the 180 µl of culture medium to obtain a final volume of 200 µl. Background plate containing the same volume of medium without cells were included in each experiment. Microplates containing cells and test compounds were incubated at 37° C., 5% $CO_2$, 95% air and 100% relative humidity for 72 hours. One microplate for each cell line were fixed as described below. These four microplates represented basal growth at time zero. After incubation time of 72 hours, cells were fixed with 50 µl of cold (4° C.) 50% (w/v) trichloroacetic acid (TCA) added to the top of 200 µl of culture medium. These microplates contained conditions of growth control and test growth. Microplates were left 60 minutes at 4° C. and subsequently wash five times with 200 µl of deionized water. Microplates were left to dry at room temperature for at least 24 hours. All microplates were fixed with 100 µl of cold 0.4% (w/v) SRB dissolved in 1% acetic acid solution in water added to each well containing cells and left at room temperature for 10 minutes. Unbound SRB was removed with successive washes (five times) with 200 µl of cold 1% acetic acid solution in water. All microplates were left to dry at room temperature for at least 24 hours. Bound SRB to proteins was solubilised with the addition of 100 µl of 10 mM cold unbuffered Tris-base solution (pH 10.5). Microplates were left on a plate shaker for 5 minutes. Absorbance was read at 515 nm using a 96-well plate Multiskan Spectrum luminescence reader (Thermo Electron Corporation). Data analysis was performed using Excel 2003 and SigmaPlot 8.0 or GraphPad-Prism 3.02 software. Percent growth inhibition was calculated using the absorbance measurements [Growth at time zero ($T_0$), growth control (C) plus the test growth at the drug concentrations tested ($T_i$) as follows: $(T_i-T_0)/(C-T_0) \times 100$]. The results obtained are shown in FIGS. 1 to 4.

FIG. 1 represents the in vitro cell viability assay of six different concentrations of composition 1 on A-549 human lung cancer cell line. The positive control etoposide at 294 µg/ml shows 100% growth inhibition. The 50% growth inhibition is around 12.5 µg/ml of the tested composition.

Figure 2:
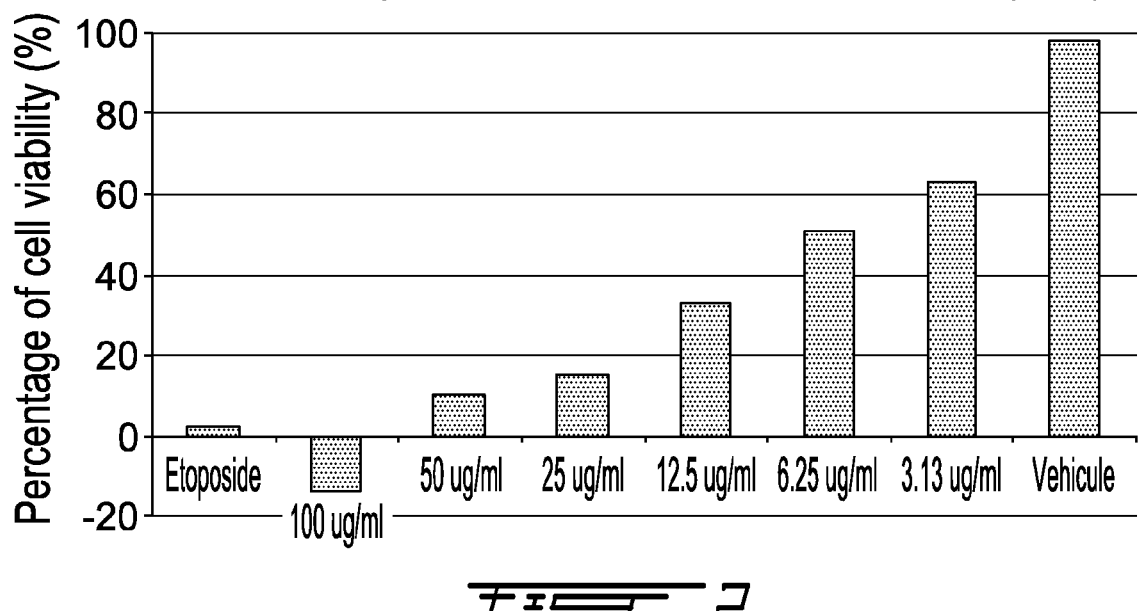
FIG. 2 is a diagram showing the results of an in vitro assay of a composition according to an embodiment of the present disclosure, wherein the assay was carried out on PC3 human cancer cell line.

FIG. 2 represents the in vitro cell viability assay of six different concentrations of composition 1 on PC-3 human prostate cancer cell line. The positive control etoposide at 294 µg/ml shows 100% growth inhibition. The 50% growth inhibition is around 6.25 µg/ml of the tested composition.

Figure 3:
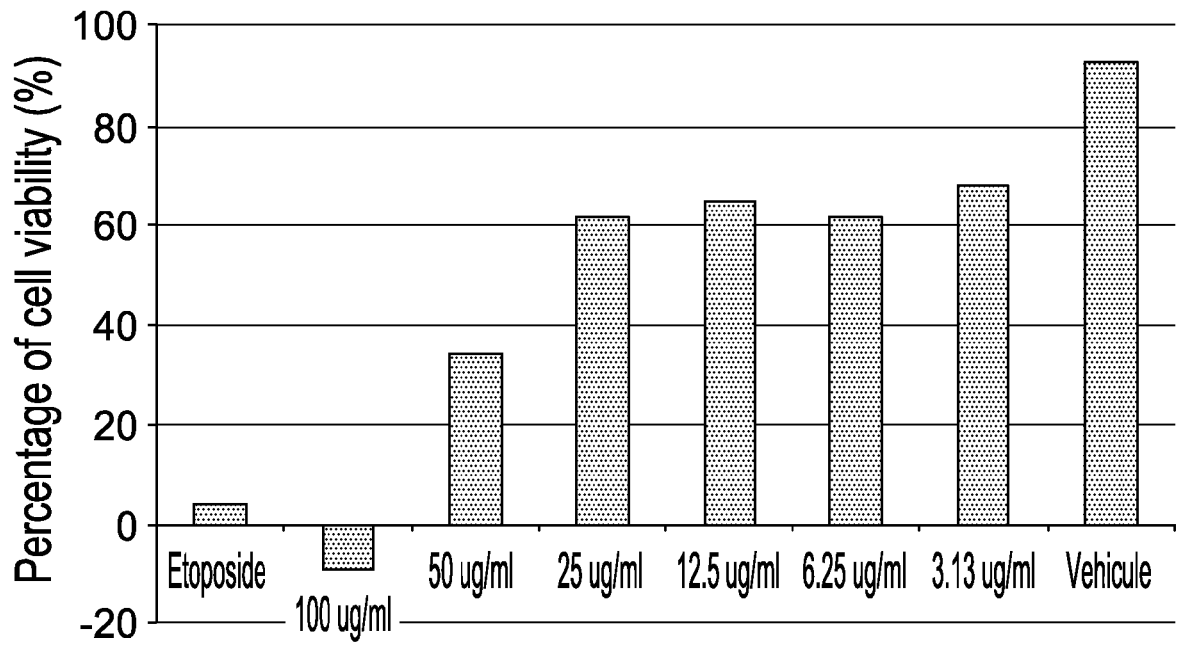
FIG. 3 is a diagram showing the results of an in vitro assay of a composition according to an embodiment of the present disclosure, wherein the assay was carried out on HCT-15 human cancer cell line.

FIG. 3 represents the in vitro cell viability assay of six different concentrations of composition 1 on HCT-15 human colon cancer cell line. The positive control etoposide at 294 µg/ml shows 100% growth inhibition. The 50% growth inhibition is around 50 µg/ml of the tested composition.

Figure 4:
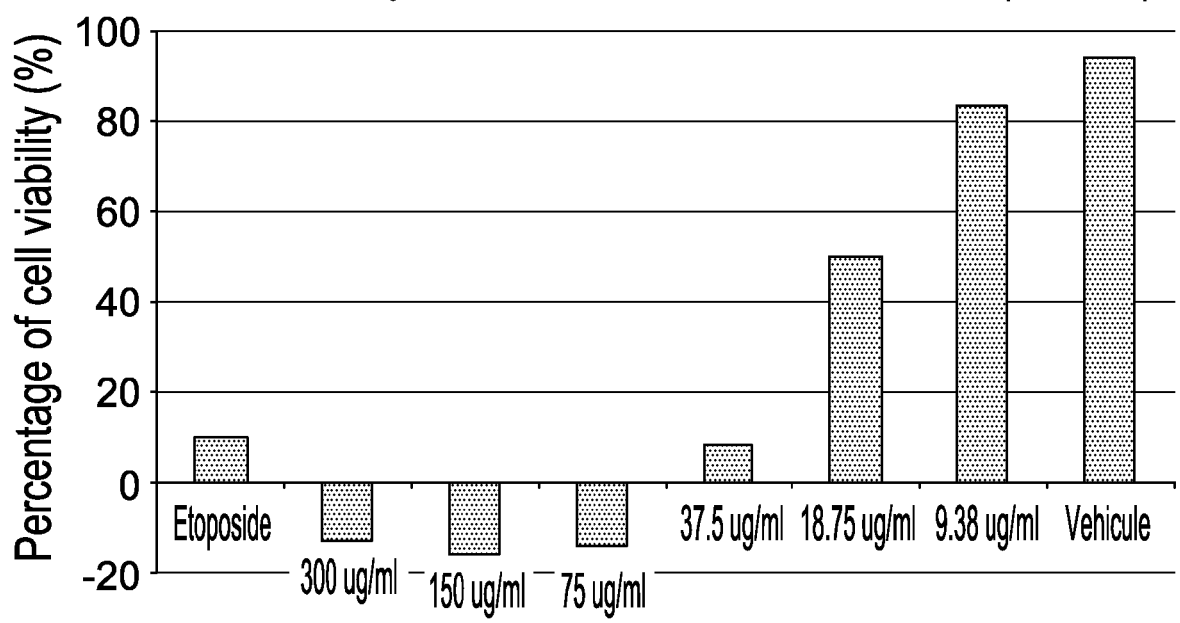
FIG. 4 is a diagram showing the results of an in vitro assay of a composition according to an embodiment of the present disclosure, wherein the assay was carried out on BT-549 human cancer cell line.

FIG. 4 represents the in vitro cell viability assay of six different concentrations of composition 1 on BT-549 human breast cancer cell line. The positive control etoposide at 294 µg/ml shows 100% growth inhibition. The 50% growth inhibition is around 18.75 µg/ml of the tested composition.

The same tests have been carried out on the substantially purified compound 1 and similar results were obtained.

Example 5

The in vivo xenograft tumor model protocol use eighteen (NU/NU-Fox1 nu) mice. After 3 days of acclimatization they were identified, weighed and selected into three cohorts randomly by weight. The animals received 3 doses of treatment before inoculation of the MCF-7 cells. Dosing consisted of 0.5 mL 3 days a week for a total of 7 weeks for each cohort. The mice received a supplement of estrogen via an implant that was inserted subcutaneously in the subscapular region 48 hrs before MCF-7 cell inoculation. The animals were weighed once a week and tumors measured 2 times per week. Blood samples (150 ml) were collected once before treatment started, and subsequently every 2 weeks after cell inoculation and at termination. Plasma was collected as well as the RBC pellet, frozen and stored at −80° C. Animals were observed for appearance of tumor development. Once tumors were detected, tumor volumes were assessed using the equation: V=L (mm)×W2 (mm)/2, where W is width and L is length of the tumor. At the end of the study surviving animals were euthanized using isoflurane and cardiac puncture performed for a terminal blood collection. Once tumors were detected, tumor volumes were assessed using the equation: V=L (mm)×W2 (mm)/2, where W is width and L is length of the tumor. At the end of the study surviving animals were euthanized using isoflurane and cardiac puncture performed for a terminal blood collection. Once tumors were detected, tumor volumes were assessed using the equation: V=L (mm)×W2 (mm)/2, where W is width and L is length of the tumor. At the end of the study surviving animals were euthanized using isoflurane and cardiac puncture performed for a terminal blood collection. Each animal was ear notched to identify their individual number and their tails marked for cage number. Animals received food and water ad libitum during the study and 3 animals were housed together per cage. The results obtained are shown in FIGS. 5 and 6.

Figure 5:
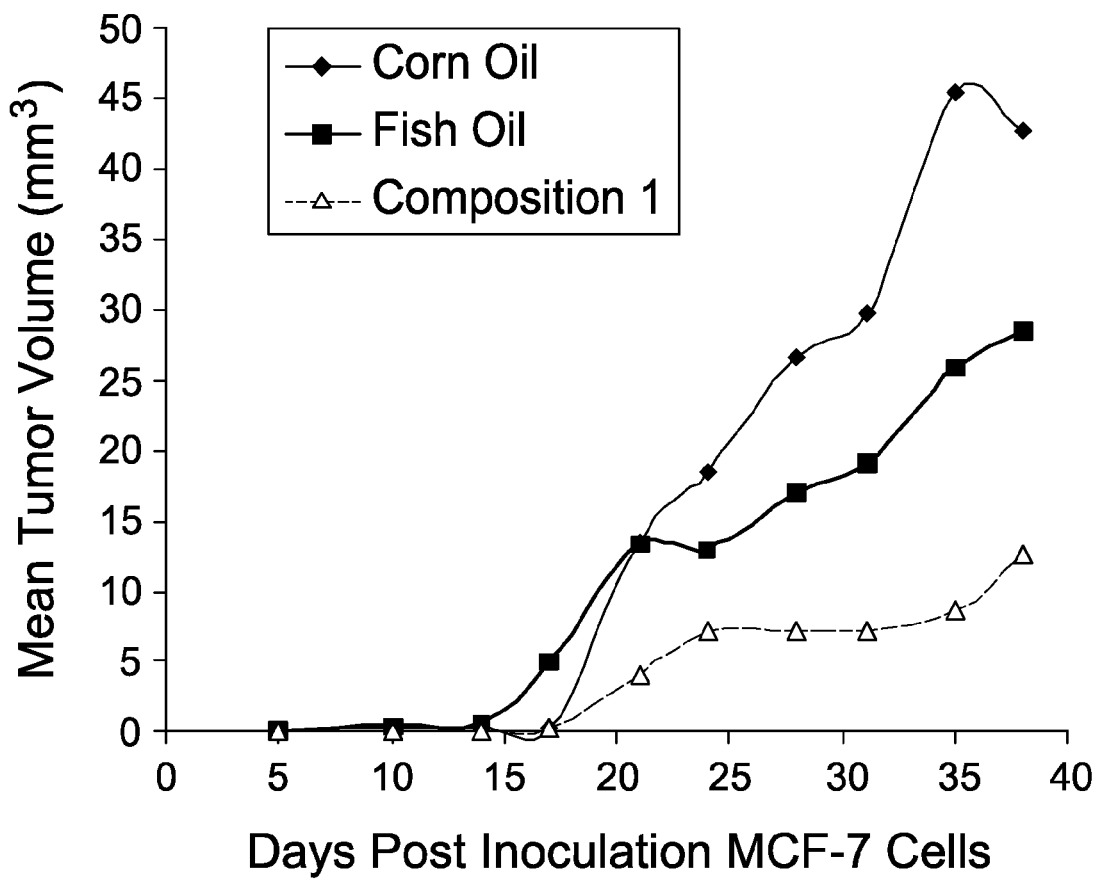
FIG. 5 is a curve representing the results of a comparative in vivo efficacy study of a composition according to an embodiment of the present disclosure, wherein the study was carried out on (NU/NU-Fox1nu) mice xenograft model.

FIG. 5 represents a comparative in vivo efficacy study of composition 1, a fish oil (pelagic fishes) and a control (corn oil), carried out on (NU/NU-Fox1nu) mice xenograft model. In both positive control (fish oil) group and composition 1 group, an altered tumor kinetics was observed. In both cases, the tumor progression was reduced and this was observed to a considerably greater extent for the composition 1 group.

Figure 6:
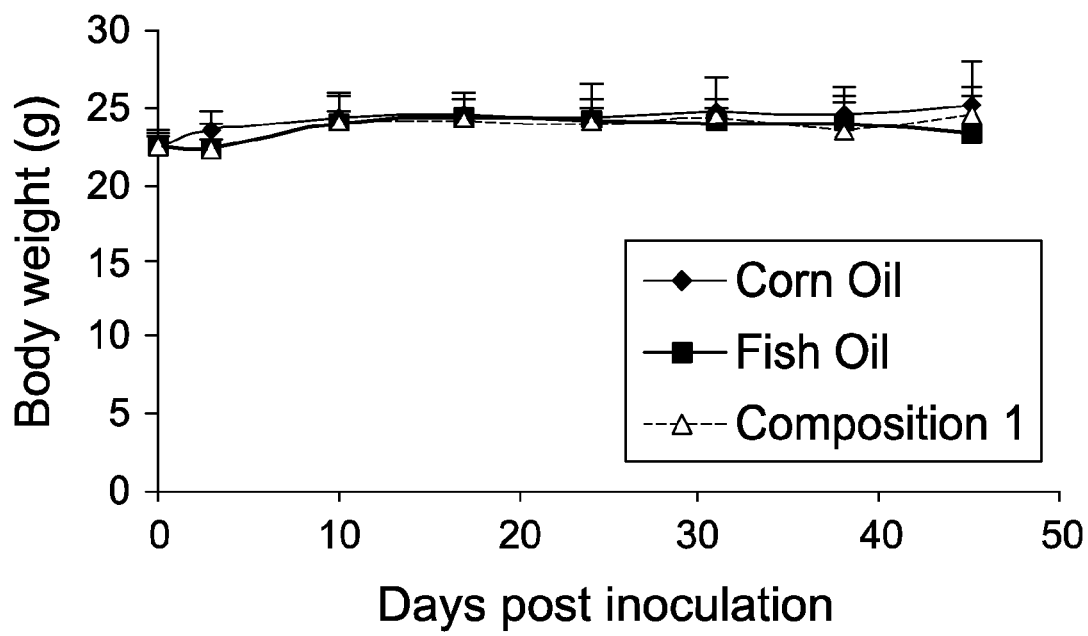
FIG. 6 is a curve representing the body weight of (NU/NU-Fox1nu) mice model as a function of days of post inoculation in the in vivo efficacy study of FIG. 5.

FIG. 6 represents the body weight of (NU/NU-Fox1nu) mice model in the in vivo efficacy study of composition 1, a fish oil and a control (corn oil). The animal body weight was not affected by any of the treatments, suggesting that no apparent toxicity was observed at these doses.

Example 6

The relative human bioavailability of two different compositions (composition 2 and a fish oil) containing docosahexaenoic acid (DHA) and omega-3 docosapentaenoic acid (DPAω3) has been determined.

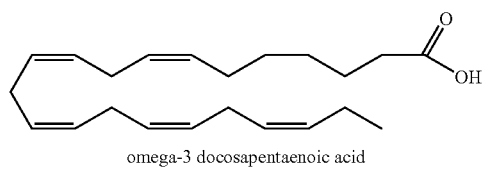

omega-3 docosapentaenoic acid

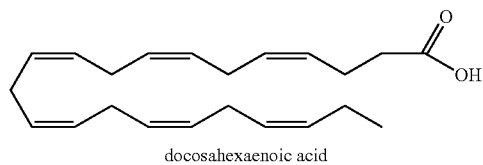

docosahexaenoic acid

The fish oil comprises compounds 2 and 7 in about a 1:8 ratio (11% of 2 and 89% of 7):

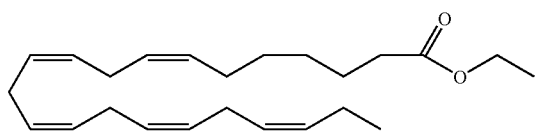

2

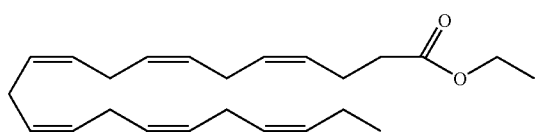

7

Composition 2 comprises compounds 1 and 5 and fish oil (comprising compounds 2 and 7 in a 1:2 ratio. In other words, composition 2 comprises compounds 1 (3.6%), 2 (7.4%), 5 (29.4%), and 7 (59.6%):

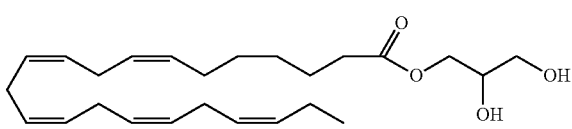

1

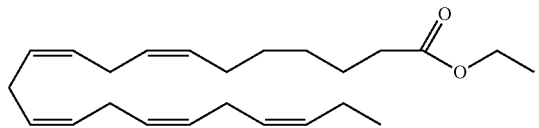

2

-continued

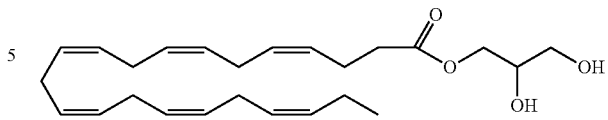

5

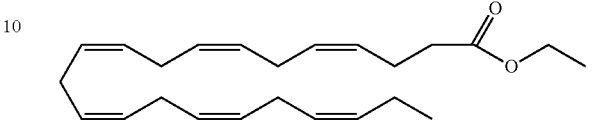

7

Composition 2 was prepared according to the same procedure as previously described in Example 2.

The relative human bioavailability of these two different compositions (composition 2 and a fish oil) was determined by a pilot cross-over study on one healthy volunteer (male). The volunteer fasted for 12 hours prior to the study. The participant consumed fish oil (capsules) equivalent to 3.0 g of DHA and 375 mg of DPAω3 as part of a breakfast. Controlled amount of boiled pasta was eaten after the 4 h time point. An initial blood sample (400 µl) was collected using a lancet at a fingertip into heparin tubes followed by samples at 1, 2, 3, 4, 5, 6, 7 and 8 hour after ingestion. Plasma was separated and immediately analysed for fatty acid composition. Fourteen days later (washout period), the procedure was repeated with composition 2 (capsules) equivalent to 3.0 g of DHA and 375 mg of DPAω3.

Figure 7:
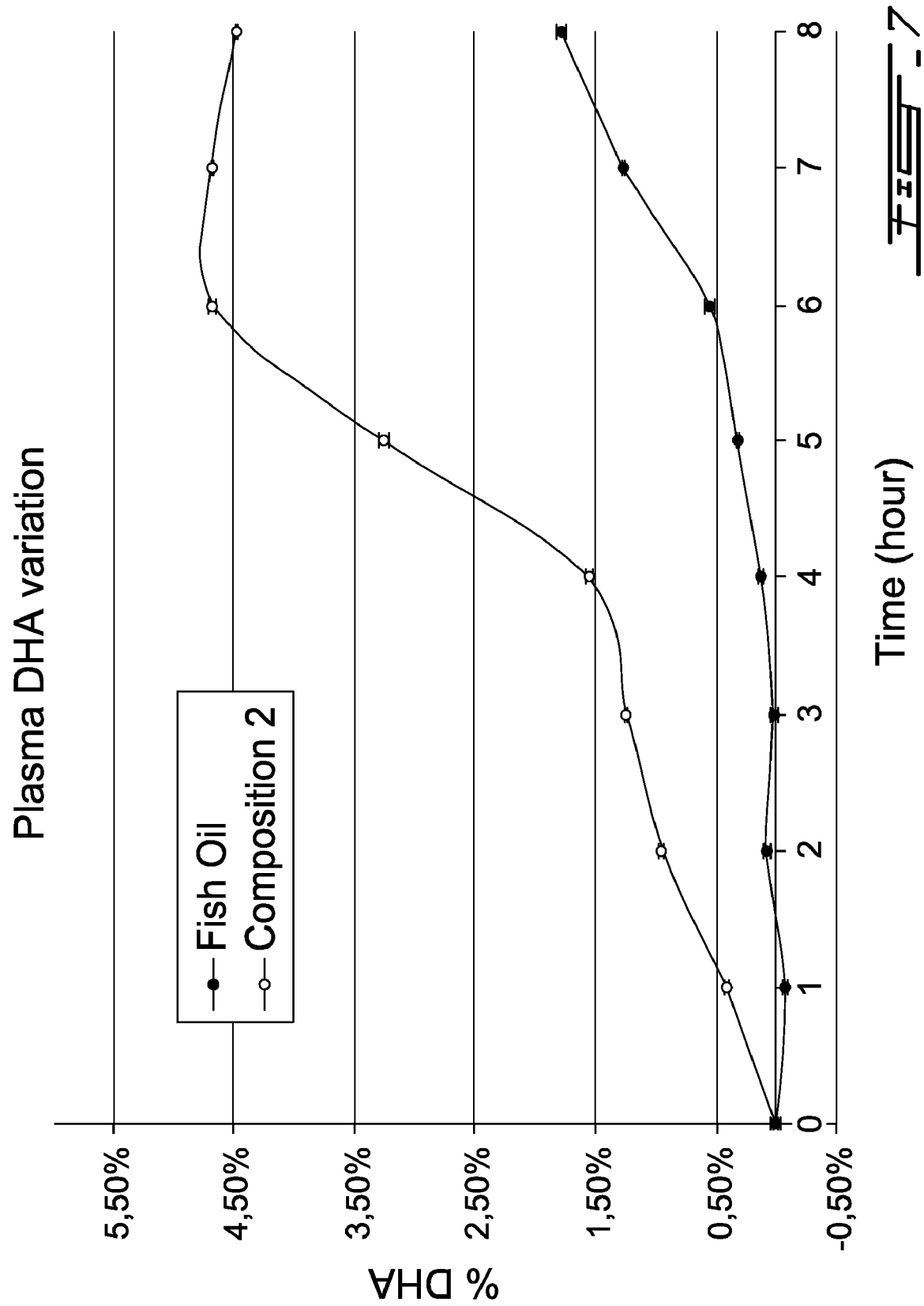
FIG. 7 represents a comparative human absorption crossover study of two different compositions containing docosahexaenoic acid (DHA) which are a fish oil and a composition according to another example.
Figure 8:
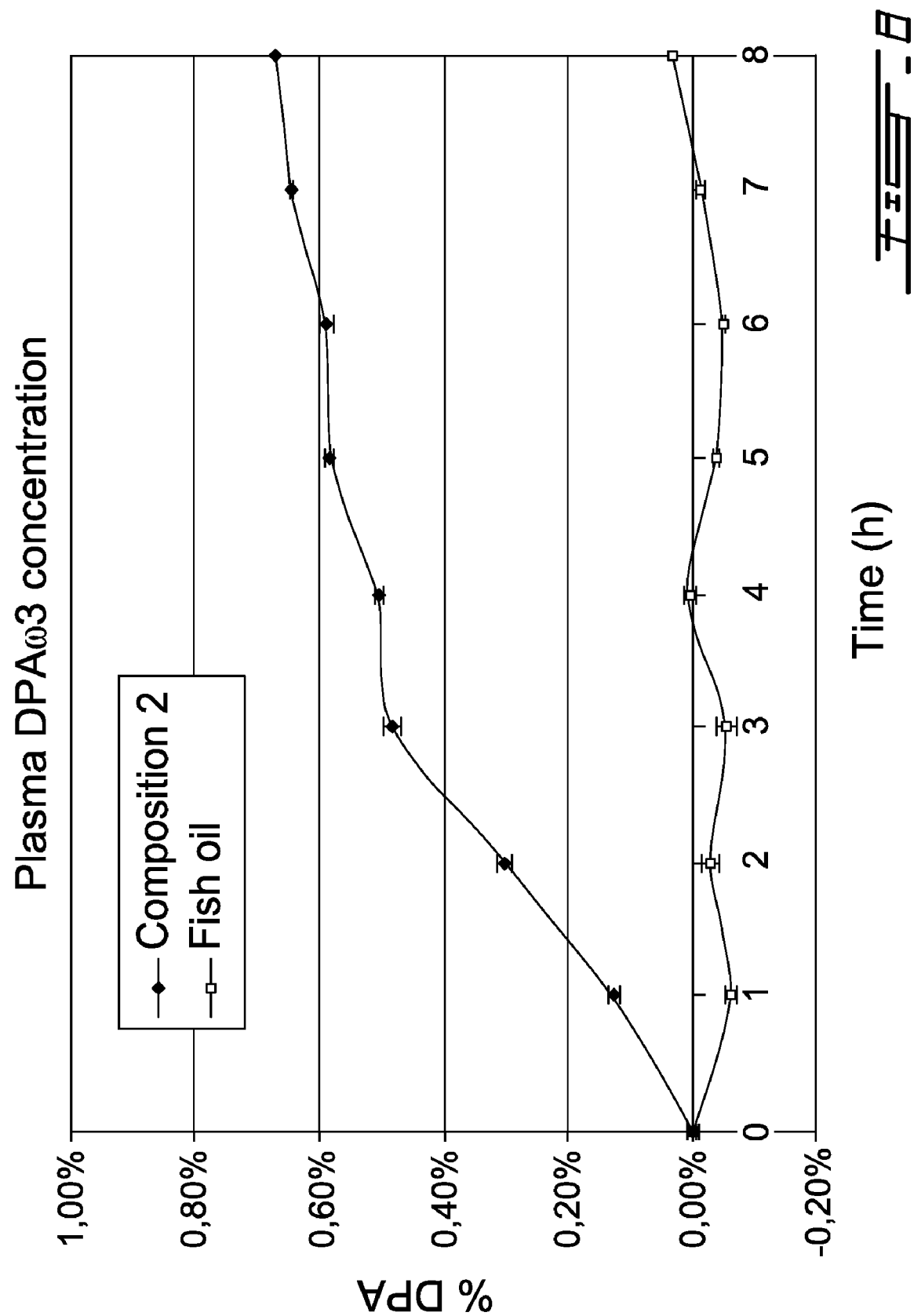
FIG. 8 represents a comparative human absorption crossover study of two different compositions containing omega-3 docosapentaenoic acid (DPAω3) which are a fish oil and a composition according to another example.

The results of this study are shown in FIGS. 7 and 8.

FIG. 7 shows the change in plasma docosahexaenoic acid (DHA) concentration of composition 2 compared to fish oil upon time over an 8 hours study.

FIG. 8 shows the change in plasma omega-3 docosapentaenoic acid (DPAω3) concentration of composition 2 compared to fish oil upon time over an 8 hours study.

In FIG. 7 the proportion of DHA in plasma (% DHA) increased slowly only after 3 hours and reach a maximum of less than 2% after 8 hours when fish oil was taken alone. With composition 2, the DHA increased moderately right after the ingestion and after 4 hours the DHA increased rapidly to reach a plateau of more than 4.5% at 6 hours. After 8 hours the DHA variation is 4.5%.

In FIG. 8 the proportion of DPAω3 in plasma (% DPAω3) did not increase after 8 hours when fish oil was taken alone, this mean that DPAω3 was not absorbed in fish oil. With composition 2, the DPAω3 increased moderately right after the ingestion to reach a plateau of 0.5% at 3 hours. After 8 hours the DPAω3 variation was more than 0.6%

The relative bioavailability of fatty acids from composition 2 compared to fish oil is calculated with the formula:

$$\text{relative bioavailability} = \frac{[AUC]_A * dose_B}{[AUC]_B * dose_A}$$

The AUC (calculates area under the curve for concentration vs. time data) is calculated using linear trapezoidal rule. The use of the linear trapezoidal rule as a method for approximating the area under a concentration-time curve is widely accepted. In this experiment, the doses are the same. The calculated relative bioavailability of docosahexaenoic acid from composition 2 compared to fish oil from time 0 to infinity is 3.72. Thus, when DHA is in the presence of compounds 1 and/or 5, DHA is 3.72 times more bioavailable. For the relative bioavailability of DPAω3, no significant absorption was found with fish oil, compared to an increase of more than 0.6% after 8 hours with composition 2. The relative bioavailability of compound 1 and compound 5 is calculated with the same formula:

$$\text{relative bioavailability} = \frac{[AUC]_A * dose_B}{[AUC]_B * dose_A}$$

The calculated relative bioavailability of compound 1 compared to compound 5 from time 0 to infinity is 2.20. Thus, compound 1 is 2.2. times more bioavailable than compounds 5.

The compounds and compositions of the present disclosure can be used for enhancing bioavailability of at least one active agent. For example, the at elast one active agent can be a fatty acid or a derivative thereof (for example an C1-C6 ester (C1-C6 being the amount of carbon atoms in the "alcohol" portion of the ester) of a fatty acid such as an ethyl ester) or a pharmaceutically acceptable salt thereof.

According to another aspect, there is provided a method for enhancing bioavailability of at least one active agent. The method comprises mixing the at least one active agent with at least one compound of the present disclosure. For example, the at least one active agent can be a lipophilic active agent such as a fatty acid or a derivative thereof (for example an C1-C6 ester (C1-C6 being the amount of carbon atoms in the "alcohol" portion of the ester) of a fatty acid such as an ethyl ester) or a pharmaceutically acceptable salt thereof.

According to another aspect, there is provided a method for enhancing bioavailability of at least one active agent. The method comprises administering to a subject an effective amount of the at least one active agent and an effective amount of at least one compound of the present disclosure. For example, the at least one active agent can be a lipophilic active agent such as a fatty acid or a derivative thereof (for example an C1-C6 ester (C1-C6 being the amount of carbon atoms in the "alcohol" portion of the ester) of a fatty acid such as an ethyl ester) or a pharmaceutically acceptable salt thereof. For example, a composition comprising an effective amount of the at least one active agent and an effective amount of at least one compound of the present disclosure can be administered. Alternatively, the effective amount of the at least one active agent and the effective amount of the at least one compound can be administered separately.

According to another aspect, there is provided a method for enhancing bioavailability of at least one active agent present in at least one oil. The method comprises administering to a subject an effective amount of the at least one oil and an effective amount of at least one compound of the present disclosure. For example, the at least one compound present in the at least one oil can be a fatty acid or a derivative thereof (for example an C1-C6 ester (C1-C6 being the amount of carbon atoms in the "alcohol" portion of the ester) of a fatty acid such as an ethyl ester) or a pharmaceutically acceptable salt thereof. For example, the oil can be a vegetable oil, fish oil, seal oil, microalgae oil, krill oil, crustacean oil (for example shrimps oil), mussels oil (for example green lipped mussels oil), or mixtures thereof. For example, a composition comprising an effective amount of the at least one oil and an effective amount of at least one compound of the present disclosure can be administered. Alternatively, the effective amount of the at least one oil and the effective amount of the at least one compound can be administered separately.

For example, the compounds of the present disclosure can be used for enhancing bioavailability of at least one compound present in a fish oil. For example, the compounds of the present disclosure can be used for enhancing bioavailability of the ethyl ester of at least one compound chosen from EPA, DPAω3, DPAω6, and DHA, and mixtures thereof.

Example 7

Composition 3 (comprising compounds 1 (11%) and 5 (89%)) at final concentration of 10 μg/ml, curcumin (5 μg/ml) and a 1:1 mixture of composition 3 (10 μg/ml) and curcumin (5 μg/ml) in DMSO (1%) was used for the in vitro assay. Composition 3 prepared according to the same procedure as previously described in Example 2)

The in vitro assay allows evaluation of the potential anti-inflammatory effects of compounds on the induced-release of pro-inflammatory mediator by monocyte cells. Typical human monocyte THP-1 cells, involved in inflammatory processes, are used in this assay. Measurement of pro-inflammatory mediator TNF-α is performed by ELISA (manufactured by R&D Systems) with artificial induction of pro-inflammatory agents by LPS (E. Coli O55:B5) during 4 hours. Known anti-inflammatory agent dexametazone was used as positive control.

Figure 9:
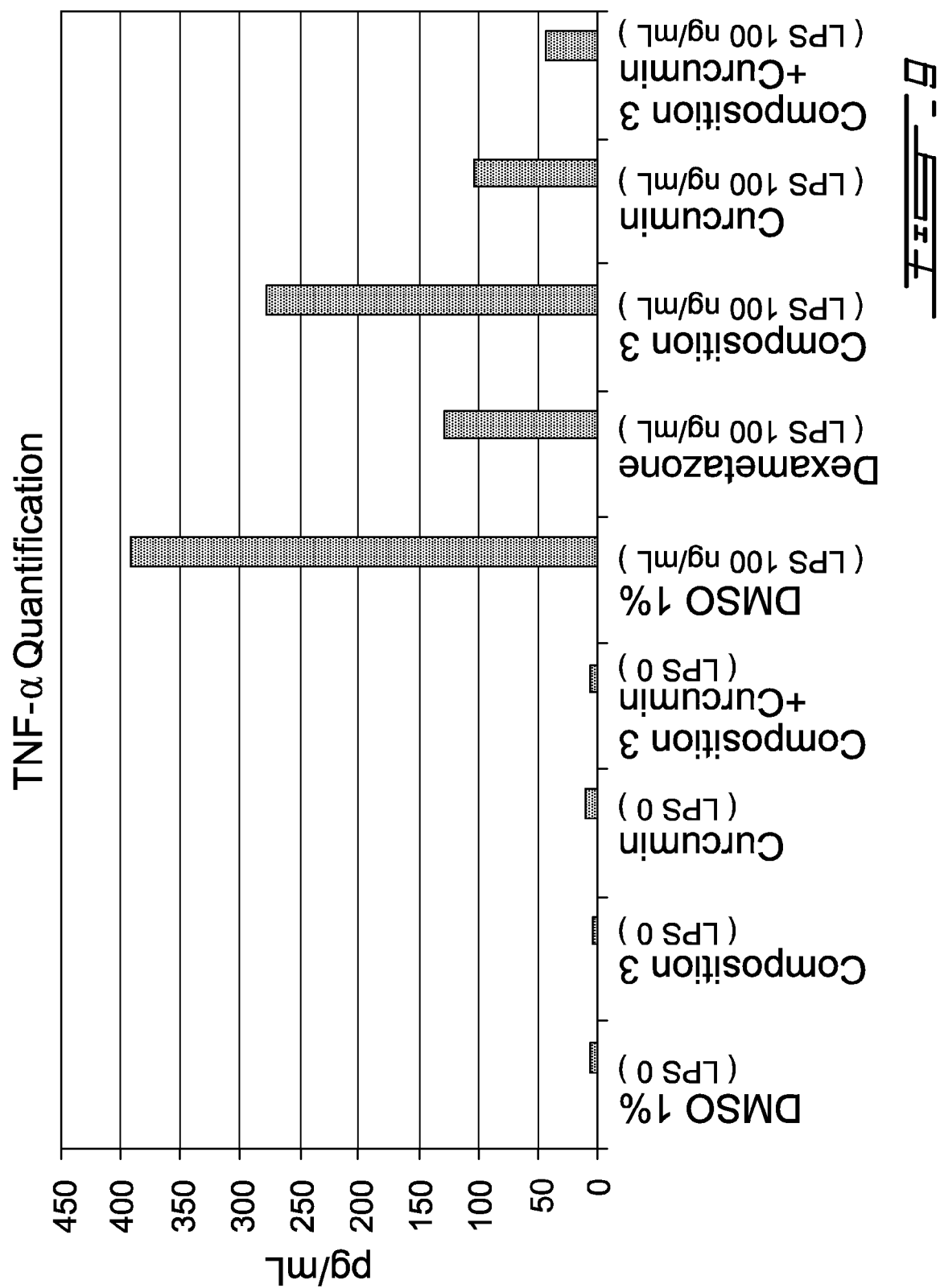
FIG. 9 represents an in vitro assay of a composition according to an example, wherein the assay was carried out on human THP-1 monocyte cell.

The results of this study are shown in FIG. 9.

In FIG. 9, no TNF-α was measured when no LPS is added to the monocyte THP-1 cells incubated with compounds or vehicle. With 100 ng/ml of LPS, 400 pg/ml of TNF-α was measured with the vehicle. With positive control dexametazone, only 125 pg/ml of TNF-α was measured, showing the anti-inflammatory effect of dexametazone. When composition 3 (10 μg/ml) was added, 275 pg/ml of TNF-α was measured and 100 pg/ml of TNF-α was measured when curcumin (5 μg/ml) is added. When a mixture of composition 3 and curcumin was added, less than 50 pg/ml of TNF-α was measured, showing a strong anti-inflammatory synergic effect.

According to another aspect, there is provided a method for treating an inflammatory disease comprising administering to a subject in need thereof an effective amount of at least one active agent and an effective amount of at least one compound of the present disclosure. For example, a composition comprising an effective amount of the at least one active agent and an effective amount of at least one compound of the present disclosure can be administered. Alternatively, the effective amount of the at least one active agent and the effective amount of the at least one compound can be administered separately.

While the disclosure has been described in connection with specific embodiments thereof, it will be understood that it is capable of further modifications and this application is intended to cover any variations, uses, or adaptations of the disclosure following, in general, the principles of the disclosure and including such departures from the present disclosure as come within known or customary practice within the art to which the disclosure pertains and as may be applied to the essential features hereinbefore set forth, and as follows in the scope of the appended claims.

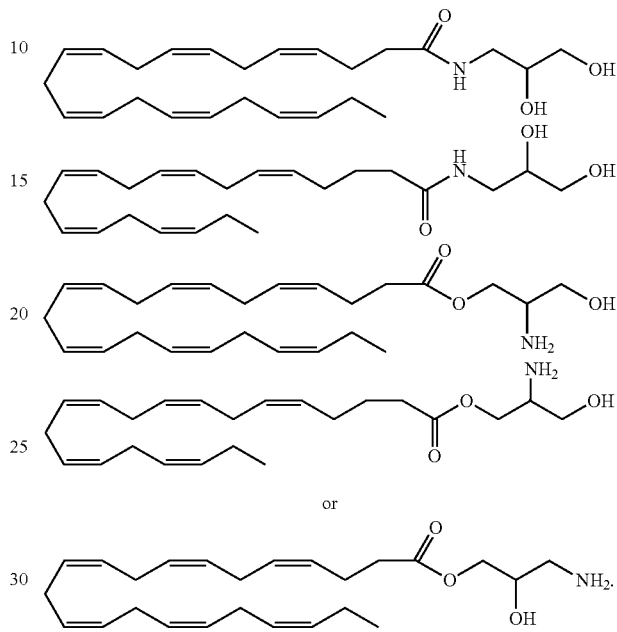

What is claimed is:

1. A compound of formula (I), (II), (III), or (IV):

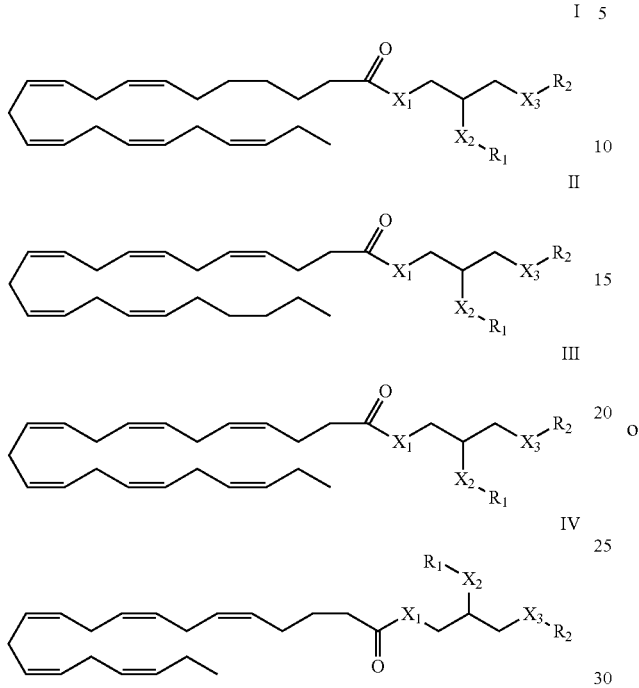

wherein
in formula (I):
X$_1$ is O, NH, or S;
X$_2$ is O, NH, or S;
X$_3$ is O, NH, or S;
R$_1$ and R$_2$ each independently represents —H, —C(O)NH$_2$, —S(O)$_2$NH$_2$, —C1-C22 (oxy)alkyl, —C1-C22 alkyl, —C1-C22 (hydroxy)alkyl, —C1-C22 (amino)alkyl, —C3-C22 alkenyl, or —C3-C22 alkynyl, formula (II):
X$_1$ is O, NH, or S;
X$_2$ is O, NH, or S;
X$_3$ is O, NH, or S;
R$_1$ and R$_2$ each independently represents —H, —C(O)NH$_2$, —S(O)NH$_2$, —S(O)$_2$NH$_2$, —C1-C22 (oxy)alkyl, —C1-C22 alkyl, —C1-C22 (hydroxy)alkyl, —C1-C22 (amino)alkyl, —C3-C22 alkenyl, or —C3-C22 alkynyl, in formula (III):
X$_1$ is O, NH, or S;
X$_2$ is O, NH, or S;
X$_3$ is O, NH, or S;
R$_1$ is chosen from —H, —C(O)NH$_2$, —S(O)NH$_2$, —S(O)$_2$NH$_2$, —C1-C22 (oxy)alkyl, —C1-C22 alkyl, —C1-C22 (hydroxy)alkyl, —C1-C22 (amino)alkyl, —C1-C22 (halo)alkyl, —C3-C22 alkenyl, and —C3-C22 alkynyl, and R$_2$ is chosen from —C(O)NH$_2$, —S(O)NH$_2$, —S(O)$_2$NH$_2$, —C1-C22 (oxy)alkyl, —C1-C22 alkyl, —C1-C22 (hydroxy)alkyl, —C1-C22 (amino)alkyl, —C1-C22 (halo)alkyl, —C3-C22 alkenyl, and —C3-C22 alkynyl, or R$_1$ is chosen from —C(O)NH$_3$, —S(O)NH$_2$, —S(O)$_2$NH$_2$, —C1-C22 (oxy)alkyl, —C1-C22 alkyl, —C1-C22 (hydroxy)alkyl, —C1-C22 (amino)alkyl, —C1-C22 (halo)alkyl, —C3-C22 alkenyl, and —C3-C22 alkynyl, and R$_2$ is chosen from —H, —C(O)NH$_2$, —S(O)NH$_2$, —S(O)$_2$NH$_2$, —C1-C22 (oxy)alkyl, —C1-C22 alkyl, —C1-C22 (hydroxy)alkyl, —C1-C22 (amino)alkyl, —C1-C22 (halo)alkyl, —C3-C22 alkenyl, and —C3-C22 alkynyl, in formula (IV):
X$_1$ is O, NH, or S;
X$_2$ is O, NH, or S;
X$_3$ is O, NH, or S;
R$_1$ is chosen from —H, —C(O)NH$_2$, —S(O)NH$_2$, —S(O)$_2$NH$_2$, —C1-C22 (oxy)alkyl, —C1-C22 alkyl, —C1-C22 (hydroxy)alkyl, —C1-C22 (amino)alkyl, —C1-C22 (halo)alkyl, —C3-C22 alkenyl, and —C3-C22 alkynyl, and R$_2$ is chosen from —C(O)NH$_2$, —S(O)NH$_2$, —S(O)$_2$NH$_2$, —C1-C22 (oxy)alkyl, —C1-C22 alkyl, —C1-C22 (hydroxy)alkyl, —C1-C22 (amino)alkyl, —C1-C22 (halo)alkyl, —C3-C22 alkenyl, and —C3-C22 alkynyl, or R$_1$ is chosen from —C(O)NH$_2$, —S(O)NH$_2$, —S(O)$_2$NH$_2$, —C1-C22 (oxy)alkyl, —C1-C22 alkyl, —C1-C22 (hydroxy)alkyl, —C1-C22 (amino)alkyl, —C1-C22 (halo)alkyl, —C3-C22 alkenyl, and —C3-C22 alkynyl, and R$_2$ is chosen from —H, —C(O)NH$_2$, —S(O)NH$_2$, —S(O)$_2$NH$_2$, —C1-C22 (oxy)alkyl, —C1-C22 alkyl, —C1-C22 (hydroxy)alkyl, —C1-C22 (amino)alkyl, —C1-C22 (halo)alkyl, —C3-C22 alkenyl, and —C3-C22 alkynyl, or a pharmaceutically acceptable salt thereof.

2. The compound of claim 1, wherein said compound is of formula (I) or (II).

3. The compound of claim 2, wherein X$_1$ is O, X$_2$ is O, and X$_3$ is O.

4. The compound of claim 3, wherein R$_1$ and R$_2$ each independently represents —H, —C1-C22 alkyl, —C3-C22 alkenyl, or —C3-C22 alkynyl.

5. The compound of claim 3, wherein R$_1$ is —H and R$_2$ is —H.

6. The compound of claim 1, wherein said compound is of formula (I) and wherein R$_1$ and R$_2$ each independently represents —H, —C1-C22 alkyl, —C3-C22 alkenyl, or —C3-C22 alkynyl.

7. The compound of claim 1, wherein said compound is of formula (II) and wherein R$_1$ and R$_2$ each independently represents —H, —C1-C22 alkyl, —C3-C22 alkenyl, or —C3-C22 alkynyl.

8. The compound of claim 1, wherein said compound is of formula (I) wherein R$_1$ and R$_2$ are H.

9. The compound of claim 1, wherein said compound is of formula (II) wherein R$_1$ and R$_2$ are H.

10. The compound of claim 1, wherein said compound is:

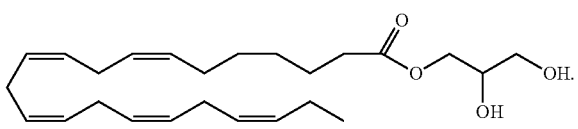

11. The compound of claim 1, wherein said compound is:

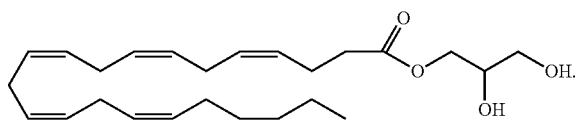

12. The compound of claim 1, wherein said compound is chosen from:

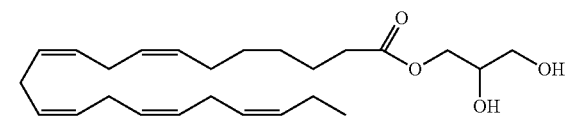

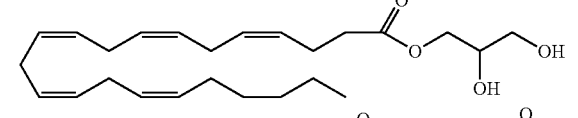

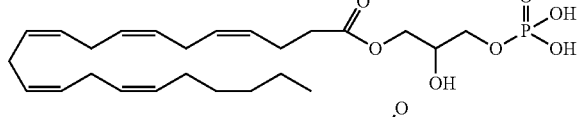

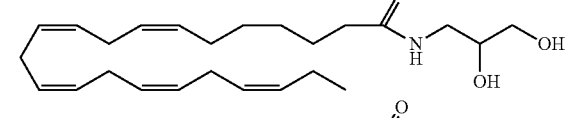

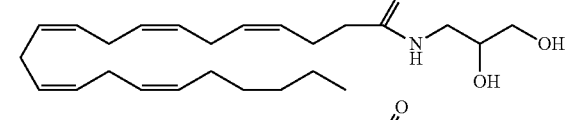

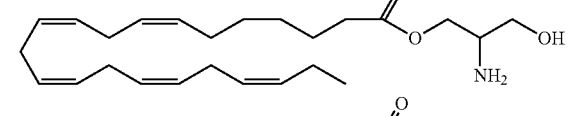

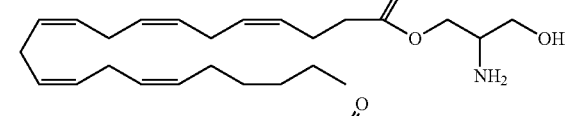

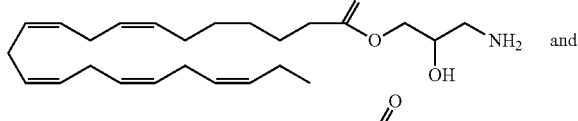

and

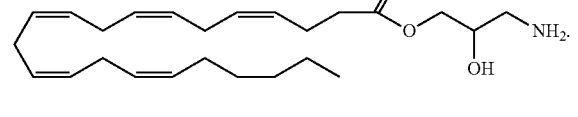

13. A composition comprising at least two compounds as defined in claim 1.

14. A composition comprising the compound of claim 10 and:

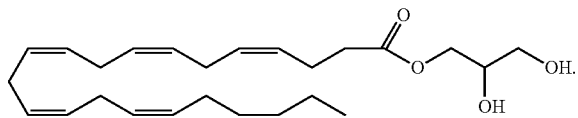

15. A composition comprising the compound of claim 10 and at least one compound chosen from:

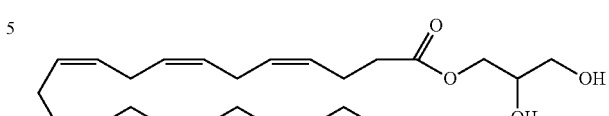

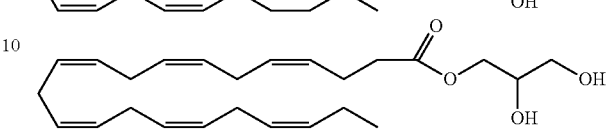

and

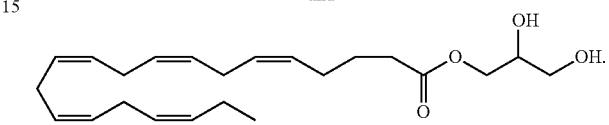

16. A compound of formula (I) or (II):

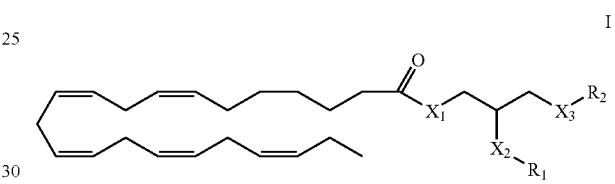

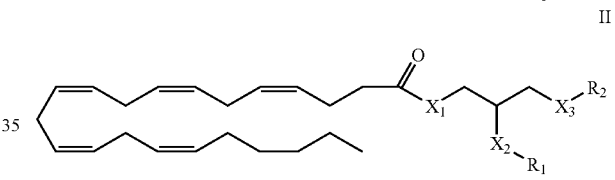

wherein
in formula (I):
X$_1$ is O, NH, or S;
X$_2$ is O, NH, or S;
X$_3$ is O, NH, or S;
R$_1$ and R$_2$ each independently represents —H, —C(O)NH$_2$, —S(O)NH$_2$, —S(O)$_2$NH$_2$, —C1-C22 (oxy)alkyl, —C1-C22 alkyl, —C1-C22 (hydroxy)alkyl, —C1-C22 (amino)alkyl, —C1-C22 (halo)alkyl, —C3-C22 alkenyl, —C3-C22 alkynyl, —(C3-C7) cycloalkyl unsubstituted or substituted with at least one substituent chosen from C1-C22 alkyl, —C2-C22 alkenyl, and —C2-C22 alkynyl, —C6-C12 aryl, —C7-C22 (aryl)alkyl, —C8-C22 (aryl)alkenyl, —C8-C22 (aryl)alkynyl, three- to seven-membered non-aromatic heterocycle unsubstituted or substituted with at least one substituent chosen from —C1-C22 alkyl, —C2-C22 alkenyl, and —C2-C22 alkynyl, five- to seven-membered aromatic heterocycle unsubstituted or substituted with at least one substituent chosen from —C1-C22 alkyl, —C2-C22 alkenyl, and —C2-C22 alkynyl, —(CH$_2$)$_n$ amino acid wherein the amino acid is connected through its alpha carbon atom, —(CH$_2$)$_n$ peptide wherein the peptide is connected through the alpha carbon atom of one of its amino acids, —CH$_2$OR$_5$, —C(O)OR$_5$, —C(O)NR$_5$, —S(O)$_2$NHR$_5$, —SOR$_5$, —S(O)$_2$R$_5$, -arylP(O)(OR$_5$)$_2$, a sugar, or a sugar phosphate
or R$_1$ and R$_2$ are joined together so as to form a five- to seven-membered non-aromatic heterocycle unsubstituted or substituted with at least one substituent chosen from —C1-C22 alkyl, —C2-C22 alkenyl, and —C2-C22 alkynyl, a phosphate, sulfate carbonyl group, or a thiocarbonyl imine;

R$_5$ is —H, —C1-C22 alkyl, —(C3-C7) cycloalkyl, —C1-C22 (halo)alkyl, —C6-C12 aryl, —C2-C22 alkenyl, —C2-C22 alkynyl, —C7-C22 (aryl)alkyl, —C8-C22 (aryl)alkenyl, —C8-C22 (aryl)alkynyl, —C1-C22 (hydroxy)alkyl, —C1-C22 alkoxy, —C1-C22 (amino)alkyl, a —(C3-C7) cycloalkyl unsubstituted or substituted with at least one substituent chosen from —C1-C22 alkyl, —C2-C22 alkenyl, and —C2-C22 alkynyl, a three- to seven-membered non-aromatic heterocycle unsubstituted or substituted at least one substituent chosen from —C1-C22 alkyl, —C2-C22 alkenyl, and —C2-C22 alkynyl, a three- to seven-membered aromatic heterocycle unsubstituted or substituted with at least one substituent chosen from —C1-C22 alkyl, —C2-C22 alkenyl, and —C2-C22 alkynyl, a —(CH$_2$)$_n$ amino acid wherein the amino acid is connected to the compound through its alpha carbon atom, a —(CH$_2$)$_n$ peptide wherein the peptide is connected to the compound through the alpha carbon atom of one of its amino acids, a sugar or a sugar phosphate; and n is an integer having a value of 0, 1, 2, 3, or 4, in formula (II):

X$_1$ is O, NH, or S;
X$_2$ is O, NH, or S;
X$_3$ is O, NH, or S;

R$_1$ and R$_2$ each independently represents —H, —C(O)NH$_2$, —S(O)NH$_2$, —S(O)$_2$NH$_2$, —C1-C22 (oxy)alkyl, —C1-C22 alkyl, —C1-C22 (hydroxy)alkyl, —C1-C22 (amino)alkyl, —C1-C22 (halo)alkyl, —C3-C22 alkenyl, —C3-C22 alkynyl, —(C3-C7) cycloalkyl unsubstituted or substituted with at least one substituent chosen from C1-C22 alkyl, —C2-C22 alkenyl, and —C2-C22 alkynyl, —C6-C12 aryl, —C7-C22 (aryl)alkyl, —C8-C22 (aryl)alkenyl, —C8-C22 (aryl)alkynyl, three- to seven-membered non-aromatic heterocycle unsubstituted or substituted with at least one substituent chosen from —C1-C22 alkyl, —C2-C22 alkenyl, and —C2-C22 alkynyl, five- to seven-membered aromatic heterocycle unsubstituted or substituted with at least one substituent chosen from —C1-C22 alkyl, —C2-C22 alkenyl, and —C2-C22 alkynyl, —(CH$_2$)$_n$ amino acid wherein the amino acid is connected through its alpha carbon atom, —(CH$_2$)$_n$ peptide wherein the peptide is connected through the alpha carbon atom of one of its amino acids, —CH$_2$OR$_5$, —C(O)OR$_5$, —C(O)NR$_5$, —P(O)(OR$_5$)$_2$, —S(O)$_2$NHR$_5$, —SOR$_5$, —S(O)$_2$R$_5$, -arylP(O)(OR$_5$)$_2$, a sugar, or a sugar phosphate or R$_1$ and R$_2$ are joined together so as to form a five- to seven-membered non-aromatic heterocycle unsubstituted or substituted with at least one substituent chosen from —C1-C22 alkyl, —C2-C22 alkenyl, and —C2-C22 alkynyl, a phosphate, sulfate carbonyl group, or a thiocarbonyl imine;

R$_5$ is —H, —C1-C22 alkyl, —(C3-C7) cycloalkyl, —C1-C22 (halo)alkyl, —C6-C12 aryl, —C2-C22 alkenyl, —C2-C22 alkynyl, —C7-C22 (aryl)alkyl, —C8-C22 (aryl)alkenyl, —C8-C22 (aryl)alkynyl, —C1-C22 (hydroxy)alkyl, —C1-C22 alkoxy, —C1-C22 (amino)alkyl, a —(C3-C7) cycloalkyl unsubstituted or substituted with at least one substituent chosen from —C1-C22 alkyl, —C2-C22 alkenyl, and —C2-C22 alkynyl, a three- to seven-membered non-aromatic heterocycle unsubstituted or substituted at least one substituent chosen from —C1-C22 alkyl, —C2-C22 alkenyl, and —C2-C22 alkynyl, a three- to seven-membered aromatic heterocycle unsubstituted or substituted with at least one substituent chosen from —C1-C22 alkyl, —C2-C22 alkenyl, and —C2-C22 alkynyl, a —(CH$_2$)$_n$ amino acid wherein the amino acid is connected to the compound through its alpha carbon atom, a —(CH$_2$)$_n$ peptide wherein the peptide is connected to the compound through the alpha carbon atom of one of its amino acids, a sugar or a sugar phosphate; and n is an integer having a value of 0, 1, 2, 3, or 4, or a pharmaceutically acceptable salt thereof.

17. The compound of claim 16, wherein said compound is a compound of formula:

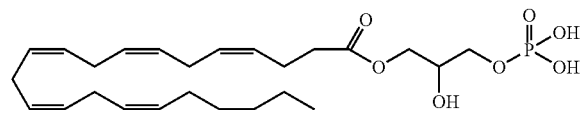

or a pharmaceutically acceptable salt thereof.

18. A compound of formula (I), (II), (III), or (IV):

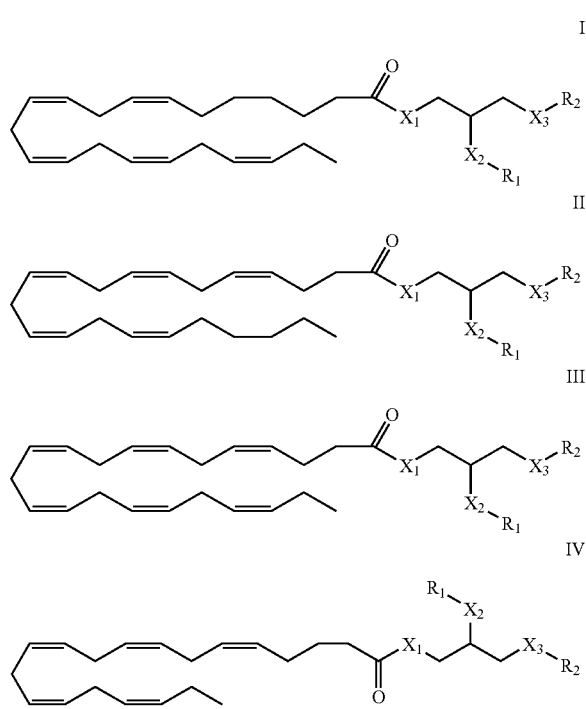

wherein in formula (I):

X$_1$ is O, NH, or S;
X$_2$ is O, NH, or S;
X$_3$ is O, NH, or S;

R$_1$ and R$_2$ each independently represents —H, —C(O)NH$_2$, —S(O)NH$_2$, —S(O)$_2$NH$_2$, —C1-C22 (oxy)alkyl, —C1-C22 alkyl, —C1-C22 (hydroxy)alkyl, —C1-C22 (amino)alkyl, —C1-C22 (halo)alkyl, —C3-C22 alkenyl, C3-C22 alkynyl, —(C3-C7) cycloalkyl unsubstituted or substituted with at least one substituent chosen from C1-C22 alkyl, —C2-C22 alkenyl, and —C2-C22 alkynyl, —C6-C12 aryl, —C7-C22 (aryl)alkyl, —C8-C22 (aryl)alkenyl, —C8-C22 (aryl)alkynyl, three- to seven-membered non-aromatic heterocycle unsubstituted or substituted with at least one substituent chosen from —C1-C22 alkyl, —C2-C22 alkenyl, and —C2-C22 alkynyl, five- to seven-membered non-aromatic heterocycle unsubstituted or substituted with at least one substituent chosen from –C1-C22 alkyl, —C2-C22 alkenyl, and —C2-C22 alkynyl, —(CH$_2$)$_n$ amino acid wherein the amino acid is connected through its alpha carbon atom, —(CH$_2$)$_n$ peptide wherein the peptide is connected through the alpha carbon atom of one of its amino acids, —CH$_2$OR$_5$, —C(O)OR$_5$, —C(O)NR$_5$, —S(O)$_2$NHR$_5$, —SOR$_5$, —S(O)$_2$R$_5$, -arylP(O)(OR$_5$)$_2$, a sugar, or a sugar phosphate or R$_1$ and R$_2$ are joined together so as to form a five- to seven-membered non-aromatic heterocycle unsubstituted or substituted with at least one substituent chosen from —C1-C22 alkyl, —C2-C22 alkenyl, and —C2-C22 alkynyl, a phosphate, sulfate carbonyl group, or a thiocarbonyl imine, R$_5$ is —H, —C1-C22 alkyl, —(C3-C7) cycloalkyl, —C1-C22 (halo)alkyl, —C6-C12 aryl, —C2-C22 alkenyl, —C2-C22 alkynyl, —C7-C22 (aryl)alkyl, —C8-C22 (aryl)alkenyl, —C8-C22 (aryl)alkynyl, —C1-C22 (hydroxy)alkyl, —C1-C22 alkoxy, —C1-C22 (amino)alkyl, a —(C3-C7) cycloalkyl unsubstituted or substituted with at least one substituent chosen from —C1-C22 alkyl, —C2-C22 alkenyl, and —C2-C22 alkynyl, a three- to seven-membered non-aromatic heterocycle unsubstituted or substituted at least one substituent chosen from —C1-C22 alkyl, —C2-C22 alkenyl, and —C2-C22 alkynyl, a three- to seven-membered aromatic heterocycle unsubstituted or substituted with at least one substituent chosen from —C1-C22 alkyl, —C2-C22 alkenyl, and —C2-C22 alkynyl, a —(CH$_2$)$_n$ amino acid wherein the amino acid is connected to the compound through its alpha carbon atom, a —(CH$_2$)$_n$ peptide wherein the peptide is connected to the compound through the alpha carbon atom of one of its amino acids, a sugar or a sugar phosphate; and n is an integer having a value of 0, 1, 2, 3, or 4, in formula (II):

X$_1$ is O, NH, or S;
X$_2$ is O, NH, or S;
X$_3$ is O, NH, or S;

R$_1$ and R$_2$ each independently represents —H, —C(O)NH$_2$, —S(O)NH$_2$, —S(O)$_2$NH$_2$, —C1-C22 (oxy)alkyl, —C1-C22 alkyl, —C1-C22 (hydroxy)alkyl, —C1-C22 (amino)alkyl, —C1-C22 (halo)alkyl, —C3-C22 alkenyl, —C3-C22 alkynyl, —(C3-C7) cycloalkyl unsubstituted or substituted with at least one substituent chosen from C1-C22 alkyl, —C2-C22 alkenyl, and —C2-C22 alkynyl, —C6-C12 aryl, —C7-C22 (aryl)alkyl, —C8-C22 (aryl)alkenyl, —C8-C22 (aryl)alkynyl, three- to seven-membered non-aromatic heterocycle unsubstituted or substituted with at least one substituent chosen from —C1-C22 alkyl, —C2-C22 alkenyl, and —C2-C22 alkynyl, five- to seven-membered aromatic heterocycle unsubstituted or substituted with at least one substituent chosen from —C1-C22 alkyl, —C2-C22 alkenyl, and —C2-C22 alkynyl, —(CH$_2$)$_n$ amino acid wherein the amino acid is connected through its alpha carbon atom, —(CH$_2$)$_n$ peptide wherein the peptide is connected through the alpha carbon atom of one of its amino acids, —CH$_2$OR$_5$, —C(O)OR$_5$, —C(O)NR$_5$, —P(O)(OR$_5$)$_2$, —S(O)$_2$NHR$_5$, —SOR$_5$, —S(O)$_2$R$_5$, -arylP(O)(OR$_5$)$_2$, a sugar, or a sugar phosphate or R$_1$ and R$_2$ are joined together so as to form a five- to seven-membered non-aromatic heterocycle unsubstituted or substituted with at least one substituent chosen from —C1-C22 alkyl, —C2-C22 alkenyl, and —C2-C22 alkynyl, a phosphate, sulfate carbonyl group, or a thiocarbonyl imine;

R$_5$ is —H, —C$_1$-C22 alkyl, —(C3-C7) cycloalkyl, —C1-C22 (halo)alkyl, —C6-C12 aryl, —C2-C22 alkenyl, —C2-C22 alkynyl, —C7-C22 (aryl)alkyl, —C8-C22 (aryl)alkenyl, —C8-C22 (aryl)alkynyl, —C1-C22 (hydroxy)alkyl, —C1-C22 alkoxy, —C1-C22 (amino)alkyl, a —(C3-C7) cycloalkyl unsubstituted or substituted with at least one substituent chosen from —C1-C22 alkyl, —C2-C22 alkenyl, and —C2-C22 alkynyl, a three- to seven-membered non-aromatic heterocycle unsubstituted or substituted at least one substituent chosen from —C1-C22 alkyl, —C2-C22 alkenyl, and —C2-C22 alkynyl, a three- to seven-membered aromatic heterocycle unsubstituted or substituted with at least one substituent chosen from —C1-C22 alkyl, —C2-C22 alkenyl, and —C2-C22 alkynyl, a —(CH$_2$)$_n$ amino acid wherein the amino acid is connected to the compound through its alpha carbon atom, a —(CH$_2$)$_n$ peptide wherein the peptide is connected to the compound through the alpha carbon atom of one of its amino acids, a sugar or a sugar phosphate; and n is an integer having a value of 0, 1, 2, 3, or 4, in formula (III):

X$_1$ is O, NH, or S;
X$_2$ is O, NH, or S;
X$_3$ is O, NH, or S;

R$_1$ and R$_2$ each independently represents, —H, —C(O)NH$_2$, —S(O)NH$_2$, —S(O)$_2$NH$_2$, —C1-C22 (oxy)alkyl, —C1-C22 alkyl, —C1-C22 (hydroxy)alkyl, —C1-C22 (amino)alkyl, —C1-C22 (halo)alkyl, —C3-C22 alkenyl, C3-C22 alkynyl, —(C3-C7) cycloalkyl unsubstituted or substituted with at least one substituent chosen from C1-C22 alkyl, —C2-C22 alkenyl, and —C2-C22 alkynyl, —C6-C12 aryl, —C7-C22 (aryl)alkyl, —C8-C22 (aryl)alkenyl, —C8-C22 (aryl)alkynyl, three- to seven-membered non-aromatic heterocycle unsubstituted or substituted with at least one substituent chosen from —C1-C22 alkyl, —C2-C22 alkenyl, and —C2-C22 alkynyl, five- to seven-membered aromatic heterocycle unsubstituted or substituted with at least one substituent chosen from —C1-C22 alkyl, —C2-C22 alkenyl, and —C2-C22 alkynyl, —(CH$_2$)$_n$ amino acid wherein the amino acid is connected through its alpha carbon atom, —(CH$_2$)$_n$ peptide wherein the peptide is connected through the alpha carbon atom of one of it amino acids, —CH$_2$OR$_5$, —C(O)OR$_5$, —C(O)NR$_5$, —S(O)$_2$NHR$_5$, —SOR$_5$, —S(O)$_2$R$_5$, -arylP(O)(OR$_5$)$_2$, a sugar, or a sugar phosphate, wherein when R$_1$ is —H, R$_2$ is different than —H, and when R$_2$ is —H, R$_1$ is different than —H, or R$_1$ and R$_2$ are joined together so as to form a five- to seven-membered non-aromatic heterocycle comprising at least one hetero atom chosen from nitrogen and sulfur, said heterocycle being unsubstituted or substituted with at least one substituent chosen from —C1-C22 alkyl, —C2-C22 alkenyl, and —C2-C22 alkynyl, a phosphate, sulfate carbonyl group, or a thiocarbonyl imine;

R$_5$ is —H, —C1-C22 alkyl, —(C3-C7) cycloalkyl, —C1-C22 (halo)alkyl, —C6-C12 aryl, —C2-C22 alkenyl, —C2-C22 alkynyl, —C7-C22 (aryl)alkyl, —C8-C22 (aryl)alkenyl, —C8-C22 (aryl)alkynyl, —C1-C22 (hydroxy)alkyl, —C1-C22 alkoxy, —C1-C22 (amino)alkyl, a —(C3-C7) cycloalkyl unsubstituted or substituted with at least one substituent chosen from —C1-C22 alkyl, —C2-C22 alkenyl, and —C2-C22 alkynyl, a three- to seven-membered non-aromatic heterocycle unsubstituted or substituted at least one substituent chosen from —C1-C22 alkyl, —C2-C22 alkenyl, and —C2-C22 alkynyl, a three- to seven-membered aromatic heterocycle unsubstituted or substituted with at least one substituent chosen from —C1-C22 alkyl, —C2-C22 alkenyl, and —C2-C22 alkynyl, a —(CH$_2$)$_n$ amino acid wherein the amino acid is connected to the compound through its alpha carbon atom, a —(CH$_2$)$_n$ peptide wherein the peptide is connected to the compound through the alpha carbon atom of one of its amino acids, a sugar or a sugar phosphate; and n is an integer having a value of 0, 1, 2, 3, or 4, in formula (IV):

$X_1$ is O, NH, or S;
$X_2$ is O, NH, or S;
$X_3$ is O, NH, or S;
$R_1$ and $R_2$ each independently represents, —H, —C(O)NH$_2$, —S(O)NH$_2$, —S(O)$_2$NH$_2$, —C1-C22 (oxy)alkyl, —C1-C22 alkyl, —C1-C22 (hydroxy)alkyl, —C1-C22 (amino)alkyl, —C1-C22 (halo)alkyl, —C3-C22 alkenyl, C3-C22 alkynyl, —(C3-C7) cycloalkyl unsubstituted or substituted with at least one substituent chosen from C1-C22 alkyl, —C2-C22 alkenyl, and —C2-C22 alkynyl, —C6-C12 aryl, —C7-C22 (aryl)alkyl, —C8-C22 (aryl)alkenyl, —C8-C22 (aryl)alkynyl, three- to seven-membered non-aromatic heterocycle unsubstituted or substituted with at least one substituent chosen from —C1-C22 alkyl, —C2-C22 alkenyl, and —C2-C22 alkynyl, five- to seven-membered aromatic heterocycle unsubstituted or substituted with at least one substituent chosen from —C1-C22 alkyl, —C2-C22 alkenyl, and —C2-C22 alkynyl, —(CH$_2$)$_n$ amino acid wherein the amino acid is connected through its alpha carbon atom, —(CH$_2$)$_n$ peptide wherein the peptide is connected through the alpha carbon atom of one of its amino acids, —CH$_2$OR$_5$, —C(O)OR$_5$, —C(O)OR$_5$, —S(O)$_2$NHR$_5$, —SOR$_5$, —S(O)$_2$R$_5$, -arylP(O)(OR$_5$)$_2$, a sugar, or a sugar phosphate, wherein when $R_1$ is —H, $R_2$ is different than —H, and when $R_2$ is —H, $R_1$ is different than —H, or $R_1$ and $R_2$ are joined together so as to form a five- to seven-membered non-aromatic heterocycle comprising at least one hetero atom chosen from nitrogen and sulfur, said heterocycle being unsubstituted or substituted with at least one substituent chosen from —C1-C22 alkyl, —C2-C22 alkenyl, and —C2-C22 alkynyl, a phosphate, sulfate carbonyl group, or a thiocarbonyl imine;

$R_5$ is —H, —C1-C22 alkyl, —(C3-C7) cycloalkyl, —C1-C22 (halo)alkyl, —C6-C12 aryl, —C2-C22 alkenyl, —C2-C22 alkynyl, —C7-C22 (aryl)alkyl, —C8-C22 (aryl)alkenyl, —C8-C22 (aryl)alkynyl, —C1-C22 (hydroxy)alkyl, —C1-C22 alkoxy, —C1-C22 (amino)alkyl, a —(C3-C7) cycloalkyl unsubstituted or substituted with at least one substituent chosen from —C1-C22 alkyl, —C2-C22 alkenyl, and —C2-C22 alkynyl, a three- to seven-membered non-aromatic heterocycle unsubstituted or substituted at least one substituent chosen from —C1-C22 alkyl, —C2-C22 alkenyl, and —C2-C22 alkynyi, a three- to seven-membered aromatic heterocycle unsubstituted or substituted with at least one substituent chosen from —C1-C22 alkyl, —C2-C22 alkenyl, and —C2-C22 alkynyl, a —(CH$_2$)$_n$ amino acid wherein the amino acid is connected to the compound through its alpha carbon atom, a —(CH$_2$)$_n$ peptide wherein the peptide is connected to the compound through the alpha carbon atom of one of its amino acids, a sugar or a sugar phosphate; and n is an integer having a value of 0, 1, 2, 3, or 4, or a pharmaceutically acceptable salt thereof.

19. The compound of claim 18, wherein in formula (I):

$X_1$ is O, NH, or S;
$X_2$ is O, NH, or S;
$X_3$ is O, NH, or S;
$R_1$ and $R_2$ each independently represents —H, —C(O)NH$_2$, —S(O)NH$_2$, —S(O)$_2$NH$_2$, —C1-C22 (oxy)alkyl, —C1-C22 alkyl, —C1-C22 (hydroxy)alkyl, —C1-C22 (amino)alkyl, —C1-C22 (halo)alkyl, —C3-C22 alkenyl, —C3-C22 alkynyl, —(C3-C7) cycloalkyl unsubstituted or substituted with at least one substituent chosen from C1-C22 alkyl, —C2-C22 alkenyl, and —C2-C22 alkynyl, —C6-C12 aryl, —C7-C22 (aryl)alkyl, —C8-C22 (aryl)alkenyl, —C8-C22 (aryl)alkynyl, three- to seven-membered non-aromatic heterocycle unsubstituted or substituted with at least one substituent chosen from —C1-C22 alkyl, —C2-C22 alkenyl, and —C2-C22 alkynyl, five- to seven-membered aromatic heterocycle unsubstituted or substituted with at least one substituent chosen from —C1-C22 alkyl, —C2-C22 alkenyl, and —C2-C22 alkynyl, —(CH$_2$)$_n$ amino acid wherein the amino acid is connected through its alpha carbon atom, —(CH$_2$)$_n$ peptide wherein the peptide is connected through the alpha carbon atom of one of its amino acids, —CH$_2$OR$_5$, —C(O)OR$_5$, —C(O)NR$_5$, —S(O)$_2$NHR$_5$, —SOR$_5$, —S(O)$_2$R$_5$, -arylP(O)(OR$_5$)$_2$, a sugar, or a sugar phosphate;

$R_5$ is —H, —C1-C22 alkyl, —(C3-C7) cycloalkyl, —C1-C22 (halo)alkyl, —C6-C12 aryl, —C2-C22 alkenyl, —C2-C22 alkynyl, —C7-C22 (aryl)alkyl, —C8-C22 (aryl)alkenyl, —C8-C22 (aryl)alkynyl, —C1-C22 (hydroxy)alkyl, —C1-C22 alkoxy, —C1-C22 (amino)alkyl, a —(C3-C7) cycloalkyl unsubstituted or substituted with at least one substituent chosen from —C1-C22 alkyl, —C2-C22 alkenyl, and —C2-C22 alkynyl, a three- to seven-membered non-aromatic heterocycle unsubstituted or substituted at least one substituent chosen from —C1-C22 alkyl, —C2-C22 alkenyl, and —C2-C22 alkynyl, a three- to seven-membered aromatic heterocycle unsubstituted or substituted with at least one substituent chosen from —C1-C22 alkyl, —C2-C22 alkenyl, and —C2-C22 alkynyl, a —(CH$_2$)$_n$ amino acid wherein the amino acid is connected to the compound through its alpha carbon atom, a —(CH$_2$)$_n$ peptide wherein the peptide is connected to the compound through the alpha carbon atom of one of its amino acids, a sugar or a sugar phosphate; and n is an integer having a value of 0, 1, 2, 3, or 4, in formula (II):

$X_1$ is O, NH, or S;
$X_2$ is O, NH, or S;
$X_3$ is O, NH, or S;
$R_1$ and $R_2$ each independently represents —H, —C(O)NH$_2$, —S(O)NH$_2$, —S(O)$_2$NH$_2$, —C1-C22 (oxy)alkyl, —C1-C22 alkyl, —C1-C22 (hydroxy)alkyl, —C1-C22 (amino)alkyl, —C1-C22 (halo)alkyl, —C3-C22 alkenyl, —C3-C22 alkynyl, —(C3-C7) cycloalkyl unsubstituted or substituted with at least one substituent chosen from C1-C22 alkyl, —C2-C22 alkenyl, and —C2-C22 alkynyl, —C6-C12 aryl, —C7-C22 (aryl)alkyl, —C8-C22 (aryl)alkenyl, —C8-C22 (aryl)alkynyl, three- to seven-membered non-aromatic heterocycle unsubstituted or substituted with at least one substituent chosen from —C1-C22 alkyl, —C2-C22 alkenyl, and —C2-C22 alkynyl, five- to seven-membered aromatic heterocycle unsubstituted or substituted with at least one substituent chosen from —C1-C22 alkyl, —C2-C22 alkenyl, and —C2-C22 alkynyl, —(CH$_2$)$_n$ amino acid wherein the amino acid is connected through its alpha carbon atom, —(CH$_2$)$_n$ peptide wherein the peptide is connected through the alpha carbon atom of one of its amino acids, —CH$_2$OR$_5$, —C(O)OR$_5$, —C(O)NR$_5$, —P(O)(OR$_5$)$_2$, —S(O)$_2$NHR$_5$, —SOR$_5$, —S(O)$_2$R$_5$, -arylP(O)(OR$_5$)$_2$, a sugar, or a sugar phosphate;

R$_5$ is —H, —C1-C22 alkyl, —(C3-C7) cycloalkyl, —C1-C22 (halo)alkyl, —C6-C12 aryl, —C2-C22 alkenyl, —C2-C22 alkynyl, —C7-C22 (aryl)alkyl, —C8-C22 (aryl)alkenyl, —C8-C22 (aryl)alkynyl, —C1-C22 (hydroxy)alkyl, —C1-C22 alkoxy, —C1-C22 (amino)alkyl, a —(C3-C7) cycloalkyl unsubstituted or substituted with at least one substituent chosen from —C1-C22 alkyl, —C2-C22 alkenyl, and —C2-C22 alkynyl, a three- to seven-membered non-aromatic heterocycle unsubstituted or substituted at least one substituent chosen from —C1-C22 alkyl, —C2-C22 alkenyl, and —C2-C22 alkynyl, a three- to seven-membered aromatic heterocycle unsubstituted or substituted with at least one substituent chosen from —C1-C22 alkyl, —C2-C22 alkenyl, and —C2-C22 alkynyl, a —(CH$_2$)$_n$ amino acid wherein the amino acid is connected to the compound through its alpha carbon atom, a —(CH$_2$)$_n$ peptide wherein the peptide is connected to the compound through the alpha carbon atom of one of its amino acids, a sugar or a sugar phosphate; and n is an integer having a value of 0, 1, 2, 3, or 4, in formula (III):

X$_1$ is O, NH, or S;
X$_2$ is O, NH, or S;
X$_3$ is O, NH, or S;
R$_1$ and R$_2$ each independently represents, —H, —C(O)NH$_2$, —S(O)NH$_2$, —S(O)$_2$NH$_2$, —C1-C22 (oxy)alkyl, —C1-C22 alkyl, —C1-C22 (hydroxy)alkyl, —C1-C22 (amino)alkyl, —C1-C22 (halo)alkyl, —C3-C22 alkenyl, C3-C22 alkynyl, —(C3-C7) cycloalkyl unsubstituted or substituted with at least one substituent chosen from C1-C22 alkyl, —C2-C22 alkenyl, and —C2-C22 alkynyl, —C6-C12 aryl, —C7-C22 (aryl)alkyl, —C8-C22 (aryl)alkenyl, —C8-C22 (aryl)alkynyl, three- to seven-membered non-aromatic heterocycle unsubstituted or substituted with at least one substituent chosen from —C1-C22 alkyl, —C2-C22 alkenyl, and —C2-C22 alkynyl, five- to seven-membered aromatic heterocycle unsubstituted or substituted with at least one substituent chosen from —C1-C22 alkyl, —C2-C22 alkenyl, and —C2-C22 alkynyl, —(CH$_2$)$_n$ amino acid wherein the amino acid is connected through its alpha carbon atom, —(CH$_2$)$_n$ peptide wherein the peptide is connected through the alpha carbon atom of one of its amino acids, —CH$_2$OR$_5$, —C(O)OR$_5$, —C(O)NR$_5$, —S(O)$_2$NHR$_5$, —SOR$_5$, —S(O)$_2$R$_5$, -arylP(O)(OR$_5$)$_2$, a sugar, or a sugar phosphate, wherein when R$_1$ is —H, R$_2$ is different than —H, and when R$_2$ is —H, R$_1$ is different than —H;

R$_5$ is —H, —C1-C22 alkyl, —(C3-C7) cycloalkyl, —C1-C22 (halo)alkyl, —C6-C12 aryl, —C2-C22 alkenyl, —C2-C22 alkynyl, —C7-C22 (aryl)alkyl, —C8-C22 (aryl)alkenyl, —C8-C22 (aryl)alkynyl, —C1-C22 (hydroxy)alkyl, —C1-C22 alkoxy, —C1-C22 (amino)alkyl, a —(C3-C7) cycloalkyl unsubstituted or substituted with at least one substituent chosen from —C1-C22 alkyl, —C2-C22 alkenyl, and —C2-C22 alkynyl, a three- to seven-membered non-aromatic heterocycle unsubstituted or substituted at least one substituent chosen from —C1-C22 alkyl; —C2-C22 alkenyl, and —C2-C22 alkynyl; a three- to seven-membered aromatic heterocycle unsubstituted or substituted with at least one substituent chosen from —C1-C22 alkyl, —C2-C22 alkenyl, and —C2-C22 alkynyl, a —(CH$_2$)$_n$ amino acid wherein the amino acid is connected to the compound through its alpha carbon atom, a —(CH$_2$)$_n$ peptide wherein the peptide is connected to the compound through the alpha carbon atom of one of its amino acids, a sugar or a sugar phosphate; and n is an integer having a value of 0, 1, 2, 3, or 4, in formula (IV):

X$_1$ is O, NH, or S;
X$_2$ is O, NH, or S;
X$_3$ is O, NH, or S;
R$_1$ and R$_2$ each independently represents, —H, —C(O)NH$_2$, —S(O)NH$_2$, —S(O)$_2$NH$_2$, —C1-C22 (oxy)alkyl, —C1-C22 alkyl, —C1-C22 (hydroxy)alkyl, —C1-C22 (amino)alkyl, —C1-C22 (halo)alkyl, —C3-C22 alkenyl, C3-C22 alkynyl, —(C3-C7) cycloalkyl unsubstituted or substituted with at least one substituent chosen from C1-C22 alkyl, —C2-C22 alkenyl, and —C2-C22 alkynyl, —C6-C12 aryl, —C7-C22 (aryl)alkyl, —C8-C22 (aryl)alkenyl, —C8-C22 (aryl)alkynyl, three- to seven-membered non-aromatic heterocycle unsubstituted or substituted with at least one substituent chosen from —C1-C22 alkyl, —C2-C22 alkenyl, and —C2-C22 alkynyl, five- to seven-membered aromatic heterocycle unsubstituted or substituted with at least one substituent chosen from —C1-C22 alkyl, —C2-C22 alkenyl, and —C2-C22 alkynyl, —(CH$_2$)$_n$ amino acid wherein the amino acid is connected through its alpha carbon atom, —(CH$_2$)$_n$ peptide wherein the peptide is connected through the alpha carbon atom of one of its amino acids, —CH$_2$OR$_5$, —C(O)OR$_5$, —C(O)NR$_5$, —S(O)$_2$NHR$_5$, —SOR$_5$, —S(O)$_2$R$_5$, -arylP(O)(OR$_5$)$_2$, a sugar, or a sugar phosphate, wherein when R$_1$ is —H, R$_2$ is different than —H, and when R$_2$ is —H, R$_1$ is different than —H;

R$_5$ is —H, —C1-C22 alkyl, —(C3-C7) cycloalkyl, —C1-C22 (halo)alkyl, —C6-C12 aryl, —C2-C22 alkenyl, —C2-C22 alkynyl, —C7-C22 (aryl)alkyl, —C8-C22 (aryl)alkenyl, —C8-C22 (aryl)alkynyl, —C1-C22 (hydroxy)alkyl, —C1-C22 alkoxy, —C1-C22 (amino)alkyl, a —(C3-C7) cycloalkyl unsubstituted or substituted with at least one substituent chosen from —C1-C22 alkyl, —C2-C22 alkenyl, and —C2-C22 alkynyl, a three- to seven-membered non-aromatic heterocycle unsubstituted or substituted at least one substituent chosen from —C1-C22 alkyl, —C2-C22 alkenyl, and —C2-C22 alkynyl, a three- to seven-membered aromatic heterocycle unsubstituted or substituted with at least one substituent chosen from —C1-C22 alkyl, —C2-C22 alkenyl, and —C2-C22 alkynyl, a —(CH$_2$)$_n$ amino acid wherein the amino acid is connected to the compound through its alpha carbon atom, a —(CH$_2$)$_n$ peptide wherein the peptide is connected to the compound through the alpha carbon atom of one of its amino acids, a sugar or a sugar phosphate; and n is an integer having a value of 0, 1, 2, 3, or 4.

20. The compound of claim 18, wherein in formula (I):
- X$_1$ is O, NH, or S;
- X$_2$ is O, NH, or S;
- X$_3$ is O, NH, or S;
- R$_1$ and R$_2$ each independently represents —H, —C(O)NH$_2$, —S(O)$_2$NH$_2$, —C1-C22 (oxy)alkyl, —C1-C22 alkyl, —C1-C22 (hydroxy)alkyl, —C1-C22 (amino)alkyl, —C3-C22 alkenyl, or —C3-C22 alkynyl, in formula (II):
- X$_1$ is O, NH, or S;
- X$_2$ is O, NH, or S;
- X$_3$ is O, NH, or S;
- R$_1$ and R$_2$ each independently represents —H, —C(O)NH$_2$, —S(O)NH$_2$, —S(O)$_2$NH$_2$, —C1-C22 (oxy)alkyl, —C1-C22 alkyl, —C1-C22 (hydroxy)alkyl, —C1-C22 (amino)alkyl, —C3-C22 alkenyl, or —C3-C22 alkynyl, in formula (III):
- X$_1$ is O, NH, or S,
- X$_2$ is O, NH, or S;
- X$_3$ is O, NH, or S;
- R$_1$ and R$_2$ each independently represents, —C(O)NH$_2$, —S(O)NH$_2$, —S(O)$_2$NH$_2$, —C1-C22 (oxy)alkyl, —C1-C22 alkyl, —C1-C22 (hydroxy)alkyl, —C1-C22 (amino)alkyl, —C1-C22 (halo)alkyl, —C3-C22 alkenyl, or —C3-C22 alkynyl, in formula (IV):
- X$_1$ is O, NH, or S;
- X$_2$ is O, NH, or S;
- X$_3$ is O, NH, or S; and
- R$_1$ and R$_2$ each independently represents, —C(O)NH$_2$, —S(O)NH$_2$, —S(O)$_2$NH$_2$, —C1-C22 (oxy)alkyl, —C1-C22 alkyl, —C1-C22 (hydroxy)alkyl, —C1-C22 (amino)alkyl, —C1-C22 (halo)alkyl, —C3-C22 alkenyl, or —C3-C22 alkynyl.

21. The compound of claim 18, wherein said compound is: